US010940165B2

(12) United States Patent
Gottlieb et al.

(10) Patent No.: US 10,940,165 B2
(45) Date of Patent: Mar. 9, 2021

(54) ADOPTIVE T CELL THERAPY

(71) Applicants: The University of Sydney, Sydney (AU); Western Sydney Local Health District, Westmead (AU); Westmead Institute for Medical Research, Westmead (AU); NSW Health Pathology, Newcastle (AU)

(72) Inventors: David Gottlieb, Westmead (AU); Leighton Clancy, Westmead (AU); Emily Blyth, Sydney (AU); Kenneth Paul Micklethwaite, Westmead (AU); Shivashni Deo, Sydney (AU)

(73) Assignees: The University of Sydney, Sydney (AU); Western Sydney Local Health District, Westmead (AU); Westmead Institute for Medical Research, Westmead (AU); NSW Health Pathology, Newcastle (AU)

( * ) Notice: Subject to any disclaimer, the term of this patent is extended or adjusted under 35 U.S.C. 154(b) by 208 days.

(21) Appl. No.: 15/742,433

(22) PCT Filed: Jul. 7, 2016

(86) PCT No.: PCT/AU2016/050594
§ 371 (c)(1),
(2) Date: Jan. 5, 2018

(87) PCT Pub. No.: WO2017/004678
PCT Pub. Date: Jan. 12, 2017

(65) Prior Publication Data
US 2019/0070220 A1 Mar. 7, 2019

(30) Foreign Application Priority Data

Jul. 7, 2015 (AU) .................. 2015902675

(51) Int. Cl.
| | |
|---|---|
| *A61K 35/17* | (2015.01) |
| *A61K 39/00* | (2006.01) |
| *A61P 37/00* | (2006.01) |
| *A61P 31/12* | (2006.01) |
| *A61P 31/10* | (2006.01) |
| *A61K 9/00* | (2006.01) |

(52) U.S. Cl.
CPC ............ *A61K 35/17* (2013.01); *A61K 9/0019* (2013.01); *A61K 39/0002* (2013.01); *A61P 31/10* (2018.01); *A61P 31/12* (2018.01); *A61P 37/00* (2018.01); *C12N 2710/10334* (2013.01); *C12N 2760/16034* (2013.01); *Y02A 50/30* (2018.01)

(58) Field of Classification Search
None
See application file for complete search history.

(56) References Cited

PUBLICATIONS

Tintelnot et al., Medic. Mycol., 47:351-358 (2009) (Year: 2009).*
Stuehler et al., JID, 211:1251-1261 (2015) (Year: 2015).*
Tramsen et al., Cytother., 15:344-351 (2013) (Year: 2013).*
Fanci et al., Bone Marrow Transplant., 35:1215-1216 (2005) (Year: 2005).*
Rodriguez et al., Bone Marrow Transplant., 31:411-412 (2003) (Year: 2003).*
Bacher et al., Cytotherapy, 17:1396-1405 (2015) (Year: 2015).*
Deo et al., Clin. Trans. Immunol., 4:e40 (2015) (Year: 2015).*
Nucci et al, Curr. Op. Infect. Dis., 16:607-612 (2003) (Year: 2003).*
Nucci et al., CID, 38:1237-1242 (2004) (Year: 2004).*
Tramsen et al, J. Infect. Dis., 196:485-492 (2007) (Year: 2007).*
Van de Veerdonk et al., Curr. Op. Microbiol., 11:305-312 (2008) (Year: 2008).*
Extended European Search Report for Application No. 16820574.8, dated Jan. 30, 2019 (8 pages).
C. Stuehler et al: "Cross-protective TH1 immunity against Aspergillus fumigatus and Candida albicans", Blood, vol. 117, No. 22, Mar. 25, 2011 (Mar. 25, 2011), pp. 5881-5891, XP055004679, ISSN: 0006-4971, DOI: 10.1182/blood-2010-12-325084.
Shivashni S. Gaundar et al: "Robust polyfunctional T-helper 1 responses to multiple fungal antigens from a cell population generated using an environmental strain of Aspergillus fumigatus", Cytotherapy, vol. 14, No. 9, Sep. 1, 2012 (Sep. 1, 2012), pp. 1119-1130, XP055542110, GB ISSN: 1465-3249, DOI: 10.3109/14653249.2012.704013.
Deo, S. et al, "The identification and use of a three fungus-antigen combination to generate T-cell products with activity against pathogenic filamentous fungi and yeasts for clinical cell therapy" Blood, 2014, vol. 124, No. 21, 3839, published online Dec. 4, 2014.
Xiong, J. et al, "*Candida albicans* and *Candida krusei* Differentially Induce Human Blood Mononuclear Cell Interleukin-12 and Gamma Interferon Production" Infection and Immunity, 2000, vol. 68, pp. 2464-2469.
Khanna, N. et al, "Generation of a multipathogen-specific T-cell product for adoptive immunotherapy based on activation-dependent expression of CD154" Blood, 2011, vol. 118, No. 4, pp. 1121-1132.
Tramsen, L. et al, "Clinical-scale generation of human anti-*Aspergillus* T cells for adoptive immunotherapy" Bone Marrow Transplantation, 2009, vol. 43, pp. 13-19.
Lernbecher, T. "Immunotherapy of invasive fungal infection in haematopoietic stem cell transplant recipients", Frontiers in Oncology, 2013, vol. 3, 17.
Deo, S.S. et al "Stimulation with lysates of *Aspergillus terreus, Candida krusei* and *Rhizopus oryzae* maximizes cross-reactivity of antifungal T cells" Cytotherapy, 2016, vol. 18, pp. 65-79.
International Search Report for PCT/AU2016/050594, dated Sep. 21, 2016.
Written Opinion of the International Searching Authority for PCT/AU2016/050594, dated Sep. 21, 2016.

* cited by examiner

Primary Examiner — Thomas J. Visone
(74) Attorney, Agent, or Firm — K&L Gates LLP

(57) ABSTRACT

The present disclosure provides a composition comprising isolated T cells, wherein the T cells have specificity against a range of clinical fungal pathogens.

17 Claims, 12 Drawing Sheets

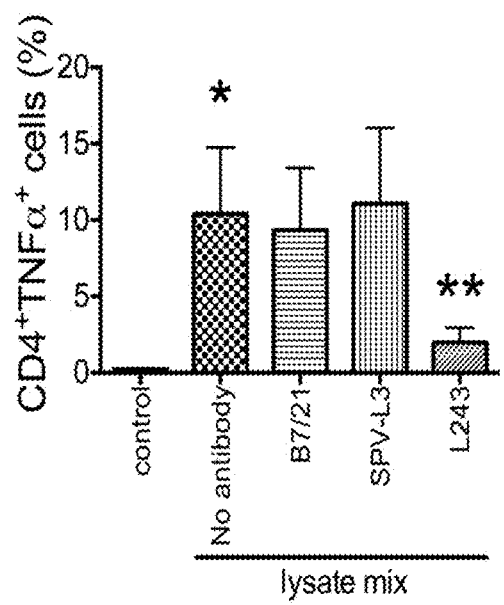
FIG. 5A
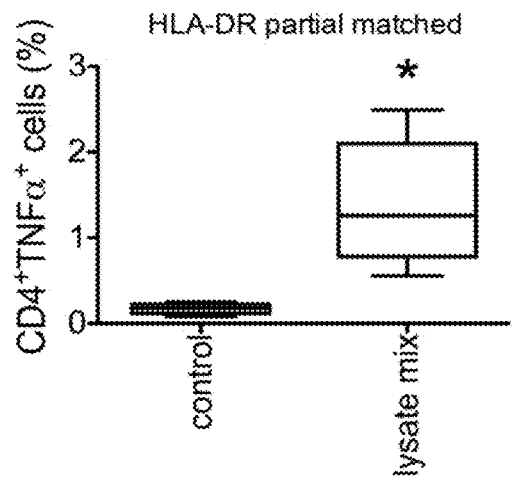 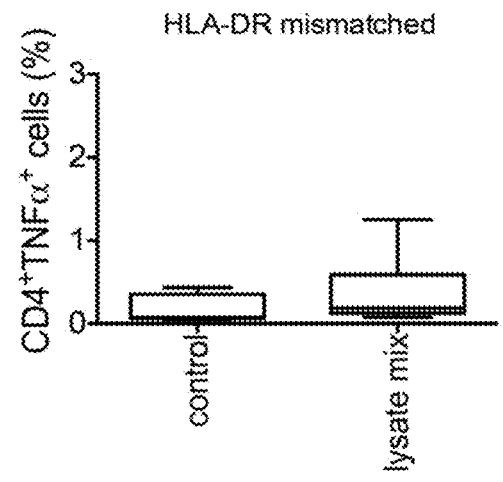
FIG. 5B          FIG. 5C

ADOPTIVE T CELL THERAPY

RELATED APPLICATION DATA

The present application is a National Stage application filed under 35 U.S.C. § 371 claiming priority to International Application No. PCT/AU2016/050594, filed on 7 Jul. 2016, which claims priority from Australian Patent Application No. 2015902675 entitled "Adoptive T Cell Therapy" filed on 7 Jul. 2015. The entire contents of each of applications which are hereby incorporated by reference.

FIELD

The present disclosure relates to T cell products with activity against fungi and yeast and uses thereof, for example, in therapy.

BACKGROUND

Invasive fungal diseases are significant causes of morbidity and mortality, particularly in patients undergoing haematological stem cell transplantation who are increasingly susceptible to infection.

The most common fungal infection seen during treatment for hematological malignancy is caused by the fungus *Aspergillus*, followed by invasive candidiasis, caused by the yeast *Candida*. Despite the introduction of better diagnostic tools and new antifungal drugs, clinical outcomes remain poor. Drug resistance is a particular problem with multiple species demonstrating resistance to Amphotericin B, and rising frequencies of azole resistance in *A. fumigatus* and *Candida* species.

T cells belong to a group of white blood cells known as lymphocytes, and play a central role in cell-mediated immunity and, to a lesser degree the adaptive immune response. Generally, T cells are distinguished from other lymphocytes (e.g., B cells and natural killer cells) by the presence of T cell receptors (TCRs). T cells have diverse roles, which are accomplished by differentiation of distinct populations of T cells, recognizable by discrete gene expression profiles. Exemplary T cell populations include naïve T cells, T helper cells ($T_H$ cells), terminally differentiated effector T cells ($T_{eff}$ cells), effector memory T cells ($T_{em}$ cells), central memory T cells ($T_{cm}$ cells), cytotoxic T cells (CTLs) and regulatory T cells (Treg cells).

Fungus-specific T cell production is fundamental to the body's defence against invasive fungal diseases, and defective in vitro T cell immunity has been shown to correlate with the period when patients are at highest risk of infection.

Adoptive immunotherapy by providing T cells specific for the fungal infection has been shown. However, T cells having cross-reactivity with multiple important fungal pathogens have not been described.

It will be clear to the skilled person from the foregoing, that there is a need in the art for restoration of effective adaptive antifungal immunity.

SUMMARY

The present disclosure is based on the inventors' identification of a panfungal T cell product with specificity against a range of clinical fungal pathogens.

The inventors isolated T cells from peripheral blood and hematopoietic stem cells mobilized with G-CSF and expanded fungus specific T cells using water soluble fungal lysates. Using these T cells, the inventors investigated those that induced cross-reactive responses against a variety of fungi. The water soluble lysates of *Aspergillus terreus* and *Candida krusei* were identified as having the broadest fungal specificity and cross-reactivity. Thus, despite, *Aspergillus fumigatus* and *Candida albicans* being the most common fungi infecting immune suppressed patients e.g., those undergoing hematopoietic stem cell transplantation, these fungi were not the lead candidates based on the approach adopted by the inventors. By looking for fungi that provided broader cross-reactive protection, the inventors of the present disclosure proceeded against conventional wisdom by not preparing T cells reactive with the fungi most commonly involved in infections. The broad cross-reactivity induced by these two fungi was not predictable.

The present disclosure is broadly directed to a composition comprising isolated T cells reactive with water soluble lysates of at least two fungi.

In one example, the disclosure provides a composition comprising isolated T cells reactive with a water soluble lysate of *A. terreus* and a water soluble lysate of *C. krusei*.

In one example, the T cells are isolated from a sample from a subject, e.g. a blood sample or fraction thereof (e.g., buffy coat fraction or peripheral blood mononuclear cell fraction) or a thymus or part thereof. Accordingly, the present disclosure also encompasses a method additionally comprising providing or obtaining a sample from a subject. Such a sample may have been isolated previously from a subject, e.g., the method is performed in vitro or ex vivo. The population of cells can also be an isolated population of cells, e.g., produced using tissue culture techniques.

In one example, the T cells are expanded, e.g., in vitro or ex vivo. For example, the isolated cells are culture expanded.

As will be apparent to the skilled artisan, the isolated and/or expanded cell population of the present disclosure is not necessarily the same as naturally-occurring T cell populations. This is because the T cells in the population are expanded against a subset of fungal antigens which does not necessarily occur together in nature. Moreover, the T cells are expanded against antigens from a combination of at least two fungi that may not occur in a subject at the same time. Furthermore, the T cells are expanded against a subset of antigens (i.e., against a subset of infective organisms) as opposed to all antigens that may occur in a subject at the same time.

In one example, the water soluble lysate is formed from cellular extracts. For example, the water soluble lysate is formed from lysed fungal spores.

Exemplary T cell populations include naïve T cells, T helper cells ($T_H$ cells), terminally differentiated effector T cells ($T_{eff}$ cells), effector memory T cells ($T_{em}$ cells), central memory T cells ($T_{cm}$ cells), cytotoxic T cells (CTLs) and regulatory T cells (Treg cells).

In one example, the composition comprises a T cell population reactive with a water soluble lysate of a first fungus and a T cell population reactive with a water soluble lysate of a second fungus.

In one example, the composition comprises a T cell population reactive with a water soluble lysate of *Aspergillus terreus*.

In one example, the composition comprises a T cell population reactive with a water soluble lysate of *Candida krusei*.

In one example, the present disclosure provides a composition comprising a combination of at least two populations of T cells, wherein a first population is reactive with a water soluble lysate of a first fungus and a second population is reactive with a water soluble lysate of a second fungus.

In one example, the present disclosure provides a composition comprising a combination of at least two populations of T cells, wherein a first population is reactive with a water soluble lysate of *A. terreus* and a second population is reactive with a water soluble lysate of *C. krusei*.

In one example, the present disclosure provides a composition comprising T cells reactive with *A. fumigatus, A. flavus, A. terreus, C. albicans, C. krusei, Fusarium oxysporum, F. solani* and *Lomentospora prolificans*.

In one example, the T cell is reactive with 1 or 2 or 3 or 4 or 5 or 6 or 7 or 8 of *A. fumigatus, A. flavus, A. terreus, C. albicans, C. krusei, F. oxysporum, F. solani* and *L. prolificans*.

In one example, the composition comprises T cells reactive with one or more additional fungi including but not limited to *A. niger, C. glabrata, C. parapsilosis, C. tropicalis, C. lusitaniae, Pneumocystis jirovecii, Cryptococcus neoformans, C. gattii, Histoplasma capsulatum* or *Stachybotrys chartarum*.

In one example, the composition comprises T cells reactive with one or more additional fungi from one or more of the genera *Alternaria, Arthrographis, Bipolaris, Chaetomium, Chrysosporium, Cladophialophora, Curvularia, Exophiala, Microsascus, Paecilomyces, Penicillium, Phialemonium, Pseudoallescheria, Schedosporium, Scopulariopsis, Trichoderma, Geotrichum, Malassezia, Rhodotorula, Saccharomyeces, Trichosporon, Zygoascus, Histoplasma, Blastomyces* or *Coccidioides*.

In one example, the composition comprises T cells reactive with one or more or all water soluble lysates selected from the group consisting of:
(i) *A. fumigatus*;
(ii) *A. flavus*;
(iii) *A. terreus*;
(iv) *C. albicans*;
(v) *C. krusei*;
(vi) *F. oxysporum*;
(vii) *F. solani*;
(viii) *L. prolificans*.

In one example, the T cell is reactive with 1 or 2 or 3 or 4 or 5 or 6 or 7 or 8 of the water soluble lysates. In one example, the composition may comprise T cells reactive with additional water soluble lysates including but not limited to those from *A. niger, C. glabrata, C. parapsilosis, C. tropicalis, C. lusitaniae, P. jirovecii, C. noeformans, C. gattii, H. capsulatum* or *S. chartarum*, or from a fungus of the genera *Alternaria, Arthrographis, Bipolaris, Chaetomium, Chrysosporium, Cladophialophora, Curvularia, Exophiala, Microsascus, Paecilomyces, Penicillium, Phialemonium, Pseudoallescheria, Schedosporium, Scopulariopsis, Trichoderma, Geotrichum, Malassezia, Rhodotorula, Saccharomyeces, Trichosporon, Zygoascus, Histoplasma, Blastomyces* or *Coccidioides*.

In one example, the present disclosure provides a composition comprising a first population of T cells reactive with *A. fumigatus, A. flavus, A. terreus, F. oxysporum, F. solani* and *L. prolificans*; and a second population of T cells reactive with *A. terreus, C. albicans*, and *C. krusei*.

In one example, the composition comprises two populations of T cells, wherein the first population of T cells is reactive with one or more or all water soluble lysates selected from the group consisting of:
(i) *A. fumigatus*;
(ii) *A. flavus*;
(iii) *A. terreus*;
(iv) *F. oxysporum*;
(v) *F. solani*; and
(vi) *L. prolificans*; and
the second population of T cells is reactive with water soluble lysates of *A. terreus, C. albicans* and *C. krusei*.

In one example, the present disclosure provides a composition additionally comprising T cells reactive with a water soluble lysate of *Rhizopus oryzae*.

In one example, the present disclosure provides a composition that does not comprise T cells produced by exposing the T cells to a water soluble lysate of *R. oryzae*.

In one example, the present disclosure provides a composition comprising T cells reactive with a water soluble lysate of *R. oryzae, C. krusei* and *F. oxysporum*.

In one example, the present disclosure provides a composition comprising T cells reactive with a water soluble lysate of *R. oryzae, C. krusei* and *L. prolificans*.

In one example, the composition comprises T cells reactive with a water soluble lysate of *R. oryzae, A. terreus* and *C. krusei*.

In one example, the present disclosure provides a composition additionally comprising T cells reactive with a water soluble extract of one or more of the following *A. fumigatus, A. flavus, C. albicans, F. oxysporum, F. solani* and/or *L. prolificans*.

In one example, the composition additionally comprises T cells reactive with 1 or 2 or 3 or 4 or 5 or 6 water soluble extracts selected from the group consisting of *A. fumigatus, A. flavus, C. albicans, F. oxysporum, F. solani* and/or *L. prolificans*. In one example, the composition additionally comprises T cells reactive with a water soluble extract of *L. prolificans*. In one example, the composition additionally comprises T cells reactive with a water soluble extract of *F. oxysporum*. In one example, the composition additionally comprises T cells reactive with a water soluble extract of *L. prolificans* and a water soluble extract of *C. krusei*. In one example, the composition additionally comprises T cells reactive with a water soluble extract of *F. oxysporum* and a water soluble extract of *C. krusei*. In one example, the composition additionally comprises T cells reactive with a water soluble extract of *L. prolificans*, a water soluble extract of *F. oxysporum* and water soluble extract of *C. krusei*.

In one example, the composition of the present disclosure has at least one of the following characteristics:
(i) at least about 80% CD3+ cells;
(ii) at least about 70% CD4+ cells;
(iii) at least about 30% terminally differentiated effector T cells;
(iv) at least about 60% effector memory T cells; and/or
(v) less than about 10% regulatory T cells.

In one example, the composition of the present disclosure comprises about 60-100% CD3+ cells, or about 70-100% CD3+ cells, or about 70-90% CD3+ cells. For example, the composition comprises about 70-80% CD3+ cells, such as about 70% CD3+ cells, or about 75% CD3+ cells, or about 80% CD3+ cells. For example, the composition comprises about 80-90% CD3+ cells, such as about 85% CD3+ cells, or about 90% CD3+ cells. For example, the composition comprises about 90-100% CD3+ cells, such as about 95% CD3+ cells, or about 100% CD3+ cells.

In one example, the percentage of CD3+ T cells is detected by flow cytometry analysis of cells expressing CD3.

In one example, the composition of the present disclosure comprises about 20-30% CD4+ cells, or about 50-100% CD4+ cells, or about 60-100% CD4+ cells, or about 60-90%

CD4+ cells. For example, the composition comprises about 60-70% CD4+ cells, such as about 60% CD4+ cells, or about 65% CD4+ cells, or about 70% CD4+ cells. For example, the composition comprises about 70-80% CD4+ cells, such as about 75% CD4+ cells, or about 80% CD4+ cells. For example, the composition comprises about 80-90% CD4+ cells, such as about 85% CD4+ cells, or about 90% CD4+ cells. For example, the composition comprises about 90-100% CD4+ cells, such as about 95% CD4+ cells, or about 100% CD4+ cells.

In one example, the percentage of CD4+ T cells is detected by flow cytometry analysis for cells expressing CD4.

In one example, the composition of the present disclosure comprises about 30-100% terminally differentiated effector T cells ($T_{eff}$ cells), for example about 30-90% $T_{eff}$ cells, or about 30-80% $T_{eff}$ cells, or about 40-70% $T_{eff}$ cells. For example, the composition comprises about 30-40% $T_{eff}$ cells, such as about 30% $T_{eff}$ cells, or about 35% $T_{eff}$ cells, or about 40% $T_{eff}$ cells. For example, the composition comprises about 40-50% $T_{eff}$ cells, such as about 45% $T_{eff}$ cells, or about 50% $T_{eff}$ cells. For example, the composition comprises about 50-60% $T_{eff}$ cells, such as about 55% $T_{eff}$ cells, or about 60% $T_{eff}$ cells. For example, the composition comprises about 60-70% $T_{eff}$ cells, or about 70-80% $T_{eff}$ cells, such as about 65% $T_{eff}$ cells, or about 70% $T_{eff}$ cells, or about 75% $T_{eff}$ cells, or about 80% $T_{eff}$ cells. For example, the composition comprises about 80-90% $T_{eff}$ cells, such as about 85% $T_{eff}$ cells, or about 90% $T_{eff}$ cells. For example, the composition comprises about 90-100% $T_{eff}$ cells, such as about 95% $T_{eff}$ cells, or about 100% $T_{eff}$ cells.

In one example, the percentage of terminally differentiated effector T cells is detected by flow cytometry analysis for cells expressing $CD3^+CD45RA^+CD62L^-$.

In one example, the composition of the present disclosure comprises about 40-100% effector memory T cells ($T_{em}$ cells), for example about 40-90% $T_{em}$ cells, or about 40-80% $T_{em}$ cells, or about 40-70% $T_{em}$ cells. For example, the composition comprises about 40-50% $T_{em}$ cells, such as about 40% $T_{em}$ cells, or about 45% $T_{em}$ cells, or about 50% $T_{em}$ cells. For example, the composition comprises about 50-60% $T_{em}$ cells, such as about 55% $T_{em}$ cells, or about 60% $T_{em}$ cells. For example, the composition comprises about 60-70% $T_{em}$ cells, or about 70-80% $T_{em}$ cells, such as about 65% $T_{em}$ cells, or about 70% $T_{em}$ cells, or about 75% $T_{em}$ cells, or about 80% $T_{em}$ cells. For example, the composition comprises about 80-90% $T_{em}$ cells, such as about 85% $T_{em}$ cells, or about 90% $T_{em}$ cells. For example, the composition comprises about 90-100% $T_{em}$ cells, such as about 95% $T_{em}$ cells, or about 100% $T_{em}$ cells.

In one example, the percentage of effector memory T cells is detected by flow cytometry analysis for cells expressing $CD3^+CD45RA^-CD62L^-$.

In one example, the composition of the present disclosure comprises less than about 20% regulatory T cells ($T_{reg}$ cells), for example less than about 15% $T_{reg}$ cells, or less than about 10% $T_{reg}$ cells. For example, the composition comprises less than about 9% $T_{reg}$ cells, such as about 8.5% $T_{reg}$ cells, or about 8% $T_{reg}$ cells, or about 7.5% $T_{reg}$ cells, or about 7% $T_{reg}$ cells, or about 6.5% $T_{reg}$ cells. For example, the composition comprises between about 3-6% $T_{reg}$ cells, such as about 6% $T_{reg}$ cells, or about 5.5% $T_{reg}$ cells, or about 5% $T_{reg}$ cells, or about 4.5% $T_{reg}$ cells, or about 4% $T_{reg}$ cells, or about 3.5% $T_{reg}$ cells, or about 3% $T_{reg}$ cells. For example, the composition comprises between about 0-6% $T_{reg}$ cells, or between about 0-3% $T_{reg}$ cells, such as about 2.5% $T_{reg}$ cells, or about 2% $T_{reg}$ cells, or about 1.5% $T_{reg}$ cells, or about 1% $T_{reg}$ cells, or about 0.5% $T_{reg}$ cells, or about 0% $T_{reg}$ cells.

In one example, the percentage of regulatory T cells is detected by flow cytometry analysis of cells expressing $CD4^+CD25^{hi}Foxp3^+$.

In one example, administration of the composition of the present disclosure to a subject confers a therapeutic or protective immune response against fungi.

In one example, the composition of the present disclosure additionally comprises isolated T cells reactive with a virus. For example, the T cells are reactive with or have been exposed to a viral antigen or cells presenting or expressing same (e.g., antigen presenting cells, such as dendritic cells, e.g., monocytic dendritic cells). Such a composition provides an advantage of conferring an immune response against not only common fungal pathogens, but also common viral pathogens.

Exemplary viruses include cytomegalovirus (CMV), Epstein-Barr virus (EBV), adenovirus (AdV), varicella zoster virus (VZV), influenza and BK virus (BKV), John Cunningham (JC) virus, respiratory syncytial virus (RSV), *parainfluenzae*, rhinovirus, human metapneumovirus, herpes simplex virus (HSV) 1, HSV II, human herpesvirus (HHV) 6, HHV 8, hepatitis A virus, hepatitis B virus, hepatitis C virus, hepatitis E virus, rotavirus, papillomavirus and parvovirus.

In one example, the composition of the disclosure additionally comprises T cells reactive with one or more viruses selected from the group consisting of CMV, EBV, AdV, VZV, influenza and BK virus, JC virus, RSV, *parainfluenzae*, rhinovirus, human metapneumovirus, HSV 1, HSV II, HHV6, HHV8, hepatitis A virus, hepatitis B virus, hepatitis C virus, hepatitis E virus, rotavirus, papillomavirus and parvovirus and mixtures thereof.

In one example, the composition comprises T cells reactive with CMV pp65.

In one example, the composition comprises T cells reactive with EBV BZLF1, LMP2A and/or EBNA1.

In one example, the composition comprises T cells reactive with CMV and EBV.

In one example, the composition comprises T cells reactive with AdV hexon.

In one example, the composition comprises T cells reactive with CMV and AdV.

In one example, the composition comprises T cells reactive with CMV, EBV and AdV.

In one example, the composition comprises T cells reactive with BKV VP1, VP2, STA and/or LTA.

In one example, the composition comprises T cells reactive with the influenza virus.

In one example, the composition comprises T cells reactive with the BK virus.

In one example, the composition comprises T cells reactive with the JC virus.

In one example, the composition comprises T cells reactive with RSV.

In one example, the composition comprises T cells reactive with the *parainfluenzae* virus.

In one example, the composition comprises T cells reactive with the rhinovirus.

In one example, the composition comprises T cells reactive with the human metapneumovirus.

In one example, the composition comprises T cells reactive with HSV 1 and/or HSV II.

In one example, the composition comprises T cells reactive with the HHV6 and/or HHV8.

In one example, the composition comprises T cells reactive with hepatitis A virus and/or hepatitis B virus and/or hepatitis C virus and/or hepatitis E virus.

In one example, the composition comprises T cells reactive with the rotavirus.

In one example, the composition comprises T cells reactive with a papillomavirus.

In one example, the composition comprises T cells reactive with a parvovirus.

The present disclosure is directed to a method for producing the composition of the present disclosure, the method comprising contacting a population of cells comprising T cells with a population of cells comprising antigen presenting cells which have been previously exposed to a water soluble lysate of *A. terreus* and a water soluble lysate of *C. krusei*.

In one example, the method of the present disclosure comprises contacting the population of cells comprising antigen presenting cells with a water soluble lysate of *A. terreus* and a water soluble lysate of *C. krusei*.

In one example, the method comprises contacting a first population of cells comprising antigen presenting cells with a water soluble lysate of *A. terreus* and contacting a second population of cells comprising antigen presenting cells with a water soluble lysate of *C. krusei* and contacting the population of cells comprising T cells with the first and second populations of cells.

In one example, the method comprises contacting a first population of cells comprising T cells with the first population of cells comprising antigen presenting cells and contacting a second population of cells comprising T cells with the second population of cells comprising antigen presenting cells and combining the first and second populations of cells comprising T cells.

In one example, the method comprises contacting the population(s) of cells comprising T cells with the population(s) of cells comprising antigen presenting cells at least twice.

For example, the method comprises contacting the population(s) of cells comprising T cells with the population(s) of cells comprising antigen presenting cells on a first day and on a second day, which is about 7 days after the first day. For example, the method comprises contacting the population(s) of cells comprising T cells with the population(s) of cells comprising antigen presenting cells at a first time point and again at a second time point, wherein the second time point is about 7 days after the first time point.

In one example, the method comprises contacting the population(s) of cells comprising T cells with the water soluble lysates and subsequently contacting the population(s) of cells comprising T cells with the population(s) of cells comprising antigen presenting cells.

For example, the method comprises contacting the population(s) of cells comprising T cells with the water soluble lysates on a first day and on a second day, which is about 7 days after the first day. For example, the method comprises contacting the population(s) of cells comprising T cells with the water soluble lysates at a first time point and contacting the population(s) of cells comprising T cells with the population(s) of cells comprising antigen presenting cells at a second time point, wherein the second time point is about 7 days after the first time point.

In one example, the population(s) comprising T cells is(are) populations of peripheral blood mononuclear cells (PBMC) or G-CSF mobilized hematopoietic stem cells (HSC) or bone marrow cells.

In one example, the antigen presenting cells are dendritic cells or monocytes (e.g., activated monocytes). In one example, the antigen presenting cells are dendritic cells. In one example, the antigen presenting cells are monocytic derived dendritic cells.

In one example, the water soluble lysates are produced by lysing germinated spores of *A. terreus* and/or *C. krusei* in water and obtaining the lysate.

In one example, the water soluble lysates are obtained by homogenizing germinated spores of *A. terreus* and/or *C. krusei* in water and obtaining the lysate. For example, the homogenized lysates are clarified by centrifugation and filtration.

In one example, the method additionally comprises contacting a population of cells comprising T cells with a population of cells comprising antigen presenting cells which have been previously exposed to a water soluble lysate of *A. fumigatus, A. flavus, C. albicans, F. oxysporum, F. solani* and *L. prolificans*.

For example, the population of cells comprising antigen presenting cells have been previously exposed to a water soluble lysate of *A. terreus, C. krusei* and *F. oxysporum*.

For example, the population of cells comprising antigen presenting cells have been previously exposed to a water soluble lysate of *A. terreus, C. krusei* and *L. prolificans*.

In one example, the method additionally comprises contacting a population of cells comprising T cells with a population of cells comprising antigen presenting cells which have been previously exposed to a viral antigen.

In one example, the viral antigen is a viral protein or a peptide thereof. In one example, the viral antigen is contained within a lysate of a virally infected cell and/or is presented by a dendritic cell exposed to one or more of the previous viral antigens or comprising an expression construct (e.g., a plasmid or viral vector) encoding a viral antigen.

In one example, the population of cells comprising antigen presenting cells have been previously exposed to one or more viruses selected from the group consisting of CMV, EBV, AdV, VZV, influenza and BK virus, JC virus, RSV, *parainfluenzae*, rhinovirus, human metapneumovirus, HSV 1, HSV II, HHV6, HHV8, hepatitis A virus, hepatitis B virus, hepatitis C virus, hepatitis E virus, rotavirus, papillomavirus and parvovirus and mixtures thereof and/or a viral antigen thereof.

In one example, the population of cells comprising antigen presenting cells have been previously exposed to CMV pp65.

In one example, the population of cells comprising antigen presenting cells have been previously exposed to EBV BZLF1, LMP2A and/or EBNA1.

In one example, the population of cells comprising antigen presenting cells have been previously exposed to CMV and EBV or viral antigens thereof.

In one example, the population of cells comprising antigen presenting cells have been previously exposed to AdV hexon.

In one example, the population of cells comprising antigen presenting cells have been previously exposed to CMV and AdV or viral antigens thereof.

In one example, the population of cells comprising antigen presenting cells have been previously exposed to CMV, EBV and AdV or viral antigens thereof.

In one example, the population of cells comprising antigen presenting cells have been previously exposed to BKV VP1, VP2, STA and/or LTA.

In one example, the population of cells comprising antigen presenting cells have been previously exposed to the influenza virus or a viral antigen thereof.

In one example, the population of cells comprising antigen presenting cells have been previously exposed to the BK virus or a viral antigen thereof.

In one example, the composition comprises T cells reactive with the JC virus or a viral antigen thereof.

In one example, the composition comprises T cells reactive with RSV or a viral antigen thereof.

In one example, the composition comprises T cells reactive with the *parainfluenzae* virus or a viral antigen thereof.

In one example, the composition comprises T cells reactive with the rhinovirus or a viral antigen thereof.

In one example, the composition comprises T cells reactive with the human metapneumovirus or a viral antigen thereof.

In one example, the composition comprises T cells reactive with HSV 1 and/or HSV II or viral antigen(s) thereof.

In one example, the composition comprises T cells reactive with the HHV6 and/or HHV8 or viral antigen(s) thereof.

In one example, the composition comprises T cells reactive with hepatitis A virus and/or hepatitis B virus and/or hepatitis C virus and/or hepatitis E virus or viral antigen(s) thereof.

In one example, the composition comprises T cells reactive with the rotavirus or a viral antigen thereof.

In one example, the composition comprises T cells reactive with a papillomavirus or a viral antigen thereof.

In one example, the composition comprises T cells reactive with a parvovirus or a viral antigen thereof.

In one example, the method additionally comprising isolating the population(s) comprising T cells following the contacting, optionally combining the populations; and, optionally, formulating the population(s) into a pharmaceutically acceptable carrier.

In one example, the present disclosure provides a method of treating a subject in need thereof, the method comprising administering the composition of the present disclosure or the population of cells comprising T cells produced by the method of the present disclosure.

For example, the method comprises administering an effective amount of the composition of the present disclosure or the population of cells comprising T cells produced by the method of the present disclosure, such as a therapeutically effective amount of the composition of the present disclosure or the population of cells comprising T cells produced by the method of the present disclosure.

In one example, the subject is undergoing or is about to commence or has completed chemotherapy and/or hematopoietic stem cell transplantation and/or immunoablation therapy and/or solid organ transplantation and/or has an inherited familial or congenital immunodeficiency syndrome and/or has an acquired immunodeficiency syndrome and/or is receiving or has received immunosuppressive therapy for an immune mediated disease.

In one example, the subject has completed chemotherapy, e.g., a subject who has received chemotherapy for a blood cancer, such as lymphoma or leukemia.

In one example, the subject has completed hematopoietic stem cell transplantation.

In one example, the subject is receiving immunosuppressive therapy following solid organ transplantation.

In one example, the subject is about to receive or has received a solid organ transplantation, e.g., transplantation of kidney, liver, pancreas, pancreatic islets, heart, lung, small bowel or other solid organ. In one example, the subject is receiving or has received immunosuppressive therapy, antibody treatment or soluble receptor treatment or another immunomodulating treatment for an immune mediated disease, e.g., inflammatory bowel disease, rheumatoid arthritis, multiple sclerosis, hepatitis, glomerulonephritis and kidney failure, cancer, lymphoma, leukemia, myelodysplasia, myeloma.

In one example, the subject is suffering from a disease or condition.

In one example, the subject suffers from an inherited familial or congenital immunodeficiency, e.g., severe combined immune deficiency, common variable immunodeficiency, alymphocytosis, Wiskott Aldrich syndrome, ataxia telangiectasia, di George syndrome, leucocyte adhesion defects, immunoglobulin deficiency. In one example, the subject has acquired immunodeficiency through infection with the human immunodeficiency virus or another pathogenic organism that has led to incompetence of the immune system or is suffering from chronic relapsing fungal infections, e.g., chronic or relapsing oral or vaginal fungal infections such as candidiasis, chronic or relapsing fungal skin infection, chronic or relapsing fungal nail infections, chronic or relapsing fungal bronchial infections, chronic or relapsing fungal sinus infections, chronic or relapsing fungal myocardial infections, chronic or relapsing fungal cerebral infections, chronic or relapsing fungal bone infections, chronic or relapsing fungal liver infections, chronic or relapsing fungal kidney or bladder infection.

In one example, the subject suffers from a cancer, such as a blood or bone marrow cancer, for example the cancer includes multiple myeloma, leukemia, lymphoma, neuroblastoma, Ewing sarcoma, myelodysplastic syndromes and gliomas. In another example, the disease or condition is a non-malignant condition, for example thalassemia, aplastic anemia, fanconi anemia and immune deficiency syndromes. In a further example, the condition or disease is associated with infection or graft-versus host disease.

In one example, the method comprises obtaining the cells from a subject and administering the composition to the same subject. For example, the T cells are autologous to the subject.

In one example, the method comprises obtaining cells from a fully HLA matched donor (i.e., a donor who has the same HLA alleles as the subject) and administering the composition to the subject. In one example, the donor is a stem cell donor. For example, the cells are allogeneic, e.g., HLA-matched allogeneic cells.

In one example, the method comprises obtaining cells from a partially HLA matched donor (i.e., a donor who has one or more HLA alleles the same as the subject) and administering the composition to the subject. In one example, the donor is a stem cell donor. For example, the cells are allogeneic, e.g., partially HLA-matched allogeneic cells. For example, the HLA allele is HLA-DR.

In one example, the method comprises matching at least one HLA allele in the cells to at least one HLA allele in the subject and administering the composition to the subject. For example, the HLA allele is a HLA-DR allele.

In one example, the T cells are non-autologous or allogeneic to the subject.

In one example, the term "obtaining cells" from a donor encompasses obtaining the cells from a bank of donor cells. For example, HLA-matched allogeneic cells or partially HLA-matched allogeneic cells are obtained from the bank and administered to the subject.

In one example, the method comprises isolating T cells from multiple donors (e.g., healthy donors), identifying at least one HLA allele in the T cells, producing a composition according to the present disclosure and banking the composition for future use.

In one example, the method further comprises matching at least one HLA allele in the banked composition with at least one HLA allele in the subject and administering the composition to the subject. For example, the HLA allele is a HLA-DR allele.

In one example, the present disclosure provides a bank comprising a plurality of compositions of the present disclosure. For example, at least one of the HLA alleles in the T cells in each composition in the bank has been identified. In one example, the HLA is a HLA-DR allele.

In one example, the present disclosure provides a method of treating a subject in need thereof, the method comprising determining a HLA allele in the subject, matching the HLA allele to a HLA allele in T cells in a composition in the bank of the present disclosure and administering to the subject a composition comprising T cells having the same HLA allele as that in the subject.

BRIEF DESCRIPTION OF THE DRAWINGS

FIG. 2A. Expansion of T cell cultures stimulated with individual fungal lysate. Data expressed as mean±SEM (n=4). FIG. 2B. Th1 cytokine distribution of responding CD4$^+$ cells on day 21 showing percentage of cells producing IFNγ (F), TNFα (T), IL-2 (2) and combinations thereof. Bars indicate means and standard deviations (n=4).

FIG. 3A. Percentage of CD4$^+$ cells producing TNFα in response to stimulation with unexposed autologous MoDC (control) or MoDC exposed to individual or all fungal lysates. Bars represent mean and standard deviations. *$p<0.05$ compared to control; n=4. FIG. 3B. Proliferation of cultured multifungus T cells in response to fungal antigens following re-stimulation with unexposed autologous MoDC or MoDC exposed to fungal lysates.

FIG. 4A. Percent hyphal damage induced by T cells against fungal antigens. Analysis was performed in quadruplicate. FIG. 4B. Hyphal damage by T cells in combination with WBC. Analysis was performed in quadruplicate. Bars represent mean and standard deviation.

FIG. 5A-FIG. 5C are graphical representations of the antifungal cytokine responses to specific MHC class II molecules. FIG. 5A. Production of TNFα by CD4+ cells stimulated with MoDC that have been unexposed or exposed with fungal lysates and incubated with HLA-DP (B7/21), -DQ (SPV-13) or -DR (L243) blocking antibodies (n=4; *$p<0.05$ compared with control; **$p<0.05$ compared with no antibody control). FIG. 5B. Intracellular expression of TNFα in CD4+ cells stimulated with MoDC derived from an allogeneic donor matched at one HLA-DRB1 allele exposed with fungal lysates (n=7; *$p<0.05$ compared with control). FIG. 5C. Expression of TNFα in CD4+ cells stimulated with MoDC derived from HLA-DRB1 mismatched donors (n=7; *$p<0.05$). Bars represent mean and standard deviation.

DETAILED DESCRIPTION

General

Figure 1:
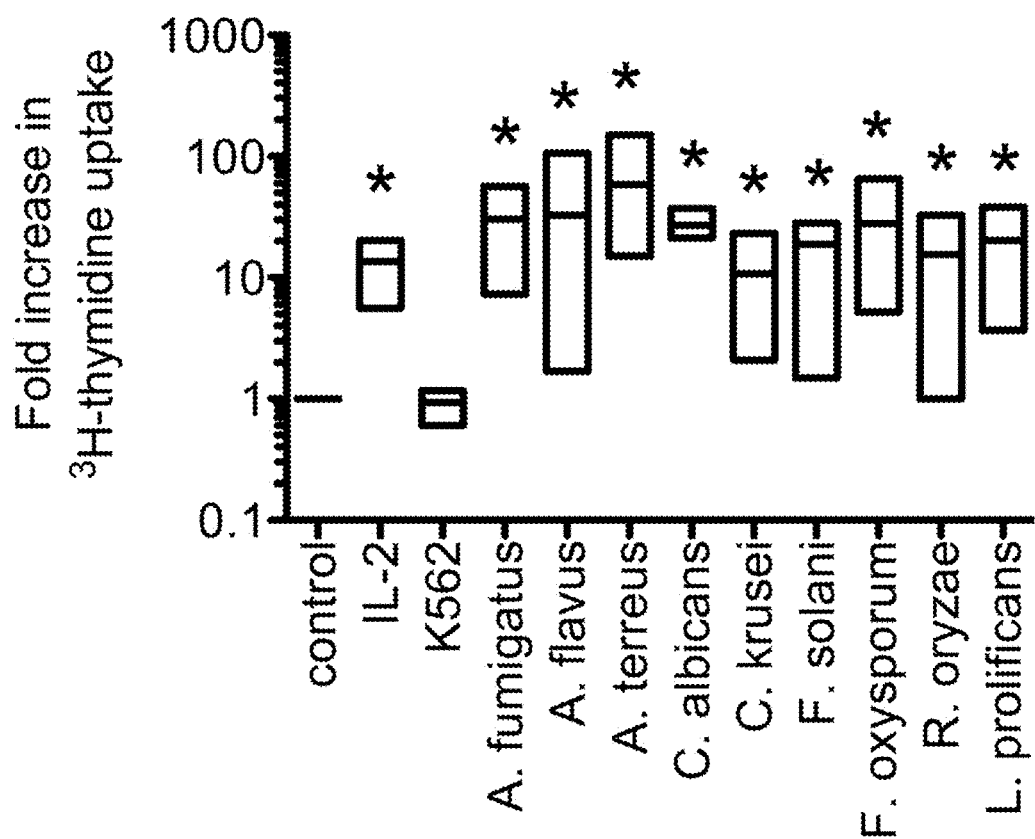
FIG. 1 is a graphical representation of the lymphoproliferative effect of fungal lysates as measured by $^3$H-thymidine uptake 7 days following stimulation. Proliferation expressed as fold increase relative to control. Analysis was performed in quadruplicate. Bars indicate mean and range (*$p<0.0$; n=3-4).

Throughout this specification, unless specifically stated otherwise or the context requires otherwise, reference to a single step, composition of matter, group of steps or group of compositions of matter shall be taken to encompass one and a plurality (i.e., one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Each example of the present disclosure described herein is to be applied mutatis mutandis to each and every other example unless specifically stated otherwise.

Those skilled in the art will appreciate that the disclosure herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the disclosure, as described herein.

The present disclosure is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in Sambrook, Fritsch & Maniatis, Molecular Cloning: A Laboratory Manual, Cold Spring Harbor Laboratories, New York, Second Edition (1989), whole of Vols I, II, and III; Benny K. C. Lo, Antibody Engineering: Methods and Protocols, (2004) Humana Press, Vol. 248; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, pp 1-22; Atkinson et al., pp 35-81; Sproat et al., pp 83-115; and Wu et al., pp 135-151; Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series; J. F. Ramalho Ortigao, "The Chemistry of Peptide Synthesis" In: Knowledge database of Access to Virtual Laboratory website (Interactiva, Germany); Sakakibara Biochem. Biophys. Res. Commun. 73: 336-342, 1976; Merrifield J. Am. Chem. Soc. 85: 2149-2154, 1963; Barany and Merrifield (1979) in The Peptides (Gross, E. and Meienhofer, J. eds.), vol. 2, pp. 1-284, Academic Press, New York. 12. Wünsch, E., ed. (1974) Synthese von Peptiden in Houben-Weyls Metoden der Organischen Chemie (Miller, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky Int. J. Peptide Protein Res. 25: 449-474, 1985; Handbook of Experimental Immunology, Vols. I-IV (D. M. Weir and C. C. Blackwell, eds., 1986, Blackwell Scientific Publications); and Animal Cell Culture: Practical Approach, 3rd edn (John R. W. Masters, ed., 2000), ISBN 0199637970, whole of text.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Selected Definitions

"T cells" belong to a group of white blood cells known as lymphocytes, and play a central role in cell-mediated immunity and, to a lesser degree the adaptive immune response. Generally, T cells are distinguished from other lymphocytes (e.g., B cells and natural killer cells) by the presence of T cell receptors (TCRs). T cells have diverse roles, which are accomplished by differentiation of distinct populations of T cells, recognizable by discrete gene expression profiles.

As used herein, the term "reactive" shall be taken to mean a T cell that is responsive to an antigen stimulus. For example, it refers to a T cell having antigenic reactivity against fungi.

The term "fungi" or "fungus", as used herein, refers to a member of a large group of eukaryotic organisms that may include microorganisms, e.g., yeasts and moulds. These organisms may be classified as a kingdom of fungi, which is separate from plants, animals, and bacteria. One major difference between fungi and the others is that fungal cells have cell walls that contain chitin, unlike the cell walls of plants, which contain cellulose.

As used herein, the terms "fungi", "fungus", or "fungal" may refer to fungi which may cause infection in humans and animals. Such fungi may also be referred to as "pathogenic fungi".

As used herein, the term "water soluble lysate" shall be taken to mean a fungal lysate that substantially dissolved in water under the conditions of temperature and concentration at which the lysate is to be used.

The term "germinated spores" as used herein shall be taken to mean a fungal spore that has been subjected to germination conditions.

As used herein, the term "obtaining the lysate" shall be taken to include the process of homogenization of the germinated fungal spores and purification of the lysate.

As used herein, the term "antigen presenting cell" refers to any cell that mediates a cellular immune response by processing and presenting antigens to the T cell receptor. In one example, the antigen presenting cell is a natural cell. For example, the antigen presenting cell is a dendritic cell or a monocyte derived dendritic cell. In one example, the antigen presenting cell is an artificially produced cell. The present disclosure also contemplates use of an artificial cell or artificial mechanism capable of initiating and enhancing the development of an immune response.

As used herein, the terms "exposed" or "exposure" or "contacting" or "contact" will be understood to mean that a population of T cells or antigen presenting cells is maintained in the presence of a water soluble fungal lysate for a time and under conditions sufficient for the antigen presenting cells to process antigens in the lysate and present them on their cell surface and/or for the T cells to become reactive with one or more fungal antigens.

The term "virus" or "viral" as used herein, refers to a small infectious agent that replicates only inside the living cells of other organisms. Exemplary viruses include cytomegalovirus (CMV), Epstein-Barr virus (EBV), adenovirus (AdV), varicella zoster virus (VZV), influenza and BK virus (BKV), John Cunningham (JC) virus, respiratory syncytial virus (RSV), *parainfluenzae*, rhinovirus, human metapneumovirus, herpes simplex virus (HSV) 1, HSV II, human herpes virus (HHV) 6, HHV 8, hepatitis A virus, hepatitis B virus, hepatitis C virus, hepatitis E virus, rotavirus, papillomavirus and parvovirus.

The term "viral antigen" as used herein refers to a protein encoded by the viral genome or a peptide derived therefrom. The viral antigen may be in the form of overlapping peptides from viral proteins, a lysate of virally infected cells. The viral antigen may also be presented by or expressed by recombinant cells (e.g., cells genetically engineered with retrovirus, lentivirus or other vectors).

As used herein the term "*mycoplasma*" refers to a genus of bacteria that lack a cell wall around their cell membrane. *Mycoplasma* can be parasitic or saprotrophic.

As used herein, the term "effective amount" shall be taken to mean a sufficient quantity of the composition to confer a therapeutic or protective immune response against fungi in a subject. The skilled artisan will be aware that such an amount will vary depending on, for example, the fungi and/or the particular subject and/or the type or severity of a condition being treated. Accordingly, this term is not to be construed to limit the disclosure to a specific quantity, for example, weight or number of population of cells of the composition of the present disclosure.

As used herein, the term "confers" shall be taken to mean that administration of the composition of the present disclosure initiates an immune response in a subject.

The term "therapeutic immune response" shall be taken to mean that administration of the composition is sufficient to induce an immune response that results in the reduction or inhibition of one or more symptoms of the infection.

The term "protective immune response" shall be taken to mean that administration of the composition is sufficient to induce an immune response that is capable of reducing or inhibiting, via IgG antibody production or T cell activation or enhancement of the actions of innate immune effectors such as monocytes, macrophages and/or neutrophils, infection by fungi.

As used herein, the term "condition" refers to a disruption of or interference with normal function, and is not to be limited to any specific condition, and will include diseases or disorders.

As used herein, the terms "treating", "treat" or "treatment" include administering a cell or cells described herein to thereby reduce or eliminate at least one symptom of a specified condition or disease.

As used herein, the term "subject" shall be taken to mean any animal, such as, a mammal. In one example, the mammal is a human or non-human primate. In one example, the mammal is a human.

As used herein, the term "donor" refers to a subject from whom cells are collected, said cells being intended for the preparation of a bank according to the present disclosure or for future preparation of a composition according to the present disclosure. The donor may be a stem cell donor from whom cells are collected as part of stem cell transplantation. Alternatively, the donor may be a solid organ donor from whom cells are collected as part of an organ transplant.

As used herein, the term "autologous" shall be taken to mean the cells are obtained from the subject that is undergoing treatment with the cells of the present disclosure.

As used herein, the term "non-autologous" shall be taken to mean the cells are from a donor. For example, the cells are obtained from a subject that is different from the subject receiving the treatment with the cells of the present disclosure.

As used herein, the term "major histocompatibility complex" or "MHC" refers to a set of cell surface molecules encoded by a large gene family in all vertebrates. MHC molecules may mediate interactions of leukocytes, also called white blood cells (WBCs), which are immune cells, with other leukocytes or body cells. MHC determines compatibility of donors for organ transplant as well as one's susceptibility to an autoimmune disease via cross-reacting immunization. In humans, MHC is also called human leukocyte antigen (HLA).

T Cell Populations

From the description herein, the skilled person will be able to identify suitable T cells for use in the present disclosure. Exemplary T cells are isolated from PBMCs, cord blood, G-CSF mobilized HSCs, bone marrow, splenic tissue, thymic tissue and lymph nodes. In one example, the T cells are isolated from PBMCs. In a further example, T cells are isolated from G-CSF mobilised HSCs. In another example, T cells are isolated from bone marrow.

Exemplary T cell populations include naïve T cells, T helper cells ($T_H$ cells), terminally differentiated effector T cells ($T_{eff}$ cells), effector memory T cells ($T_{em}$ cells), central memory T cells ($T_{cm}$ cells), cytotoxic T cells (CTLs) and regulatory T cells ($T_{reg}$ cells). Exemplary T cell populations are at least 98% T cells and less than 2% B cells and monocytes. For example, the T cells are at least $T_{eff}$ cells and $T_{em}$ cells. In an exemplary form of the disclosure, the T cells are at least about 30% $T_{eff}$, or at least about 60% $T_{em}$ cells. In one example, the T cells express at least CD3 and/or CD4. In an exemplary form of the disclosure, the T cells are at least about 80% CD3+, or at least about 70% CD4+. In one example, less than about 10% of the T cells are $T_{reg}$ cells.

Exemplary T cells are reactive with a water soluble lysate of *A. terreus* and a water soluble lysate of *C. krusei*. In one example, the T cells are produced with antigen presenting cells exposed to water soluble lysates of *A. terreus* and *C. krusei*. For example, the T cells are produced with dendritic cells, such as, monocyte derived dendritic cells (MoDC) exposed to water soluble lysates of *A. terreus* and *C. krusei*. In one example, a first T cell population is reactive with a water soluble lysate of *A. terreus* and a second population of T cells is reactive with a water soluble lysate of *C. krusei*.

In one example, the T cells are additionally reactive with a water soluble lysate of *R. orzyae*. For example, the T cell population is reactive with a water soluble lysate of *R. orzyae*, *A. terreus* and *F. oxysporum*.

In one example, the T cells are additionally reactive with a water soluble extract of *A. fumigatus*, *A. flavus*, *C. albicans*, *F. oxysporum*, *F. solani* and *L. prolificans*.

In one example, the T cells are stimulated with antigen presenting cells at defined ratios. For example, the T cells are stimulated with antigen presenting cells (APC) at APC:PBMC ratio of 1:10. In one example, the T cells are stimulated by co-culturing with antigen presenting cells with direct addition of water soluble lysates. In one example, the water soluble lysates are added at a concentration of 10 μg/ml. In one example, the PBMC and antigen presenting cells are co-cultured for a period of about 7 days.

In one example, the T cells are stimulated at least once. For example, the T cells are stimulated at least twice. For example, the T cells are stimulated twice.

In one example, a second stimulation with antigen-exposed antigen presenting cells occurs at least one or two or three or four or five or six days after the first stimulation. For example, a second stimulation with antigen-exposed antigen presenting cells occurs about 7 days after the first stimulation.

Exemplary T cells are expanded after stimulation with antigen-exposed MoDC. In one example, the T cells are expanded in cell culture. In one example, the T cells are expanded with one or more cytokines. For example, the T cells are expanded with interleukin-2 (IL-2). For example, the T cells are expanded with interleukin-15 (IL-15). For example, the T cells are expanded with interleukin-7 (IL-7). For example, the cells are expanded with IL-2, IL-15 and IL-7.

In one example, the T cells are cultured in AIM-V™ medium. In one example, the AIM-V™ medium is supplemented with 20 U/ml IL-2, 10 ng/ml IL-15 and 10 ng/ml IL-7 from about day 7 onwards. In one example, the concentration of IL-2 is increased to 50 U/ml from about day 14 onwards.

In one example, the cultures are replenished about 2, or about 3 times per week using fresh medium containing the appropriate concentration of cytokines. Exemplary T cell cultures are maintained for a total of about 21 days. In one example, cell numbers are determined by counting in a haemocytometer.

Exemplary T cells are cultured without isolation or isolated after stimulation. In one example, the T cells are isolated about 5 hours after the first stimulation. In one example, the T cells are isolated about 5 hours after the second stimulation. Methods for isolation of the T cells will be apparent to the skilled person. In one example, the T cells are isolated using the MACS™ TNFα cell enrichment kit. In one example, the T cells are expanded after isolation. In one example, the T cells are expanded for a period of about 14 days. For example, the T cells are expanded with medium supplemented with cytokines as described above.

Exemplary T cells are cross-reactive with at least the fungal antigens from a lysate of *A. fumigatus*, *A. flavus*, *C. albicans*, *F. oxysporum*, *F. solani* and *L. prolificans*. In one example, a first population of T cells is reactive with *A. fumigatus, A. flavus, F. oxysporum, F. solani* and *L. prolificans* and a second population of T cells is reactive with *A. terreus, C. albicans* and *C. krusei*.

In one example, the T cells produce TNFα at least a log higher or at least 0.5% higher in response to fungal lysates derived from *A. fumigatus, A. flavus, C. albicans, F. oxysporum, F. solani, R. orzyae* and *L. prolificans*.

In one example, the T cells express Th1 cytokines. For example, the T cells express at least IFNγ and/or IL-2. Alternatively, or in addition, the T cells express RANTES, IL17, MIP-1β and/or IL-8.

In one example, the T cells are negative for bacterial and fungal contamination. For example, the T cells are negative for bacterial and fungal contamination for a period of at least 5 days.

In one example, the T cells are negative for *Mycoplasma* contamination.

In one example, the T cells are non-reactive for infectious disease markers, such as, the presence of endotoxin, hepatitis viruses A, B or C, human immunodeficiency viruses that can be present in blood.

Fungal Lysates

Exemplary fungi of the present disclosure include filamentous fungi, e.g., of the genera *Aspergillus, Fusarium, mucor/zygomycetes (Rhizopus)* and *Scedosporium/Lomentospora* species, and the yeast *Candida*. In one example, the fungus is of the *Aspergillus* genera. In one example, the fungus is yeast of the *C. krusei* genera. For example, the filamentous fungi include *A. fumigatus, A. flavus, A. terreus, F. oxysporum, F. solani, R. oryzae* and *L. prolificans*. In one example, the fungus is *A. terreus*. Exemplary yeast of the present disclosure includes *C. albicans* and *C. krusei*. In one example, the yeast is *C. krusei*.

In one example, the fungus is isolated from the environment. For example, *A. fumigatus, A. terreus* and *F. oxysporum* are isolated from the environment.

In one example, the fungus is isolated from a clinical specimen. For example, *A. fumigatus, A. terreus, F. oxysporum, F. solani, R. oryzae, L. prolificans, C. albicans, C. krusei, G. glabrata* are obtained from clinical specimens. Methods for isolating fungal lysates from clinical specimens are known in the art and described, for example, in Braedel et al. *British Journal of Haemotology*, 125: 392-399, 2004 or Gaundar et al. *Cytotherapy*, 14: 1119-1130, 2012.

In a further example, the fungus is obtained from a repository, such as the American Type Culture Collection (ATCC). For example, *A. flavus* is obtained from ATCC. In one example, the *A. flavus* is strain ATCC-204304.

In one example, a T cell of the disclosure is reactive with a fungal or yeast spore, e.g., a cultured and/or germinated spore. Methods for culturing and germinating fungal spores will be apparent to the skilled person. In one example, fungi isolated from the environment, clinical specimens or the ATCC are sub-cultured on potato dextrose agar plates for 3-7 days. Spores are removed by washing and separated from hyphal fragments by passing through 40 μm or 60 μm pore filters. Spores are germinated in potato dextrose medium for 16-72 hours at 25-37° C. with agitation at 200 rpm.

In one example, lysates of fungi or spores are produced. Methods for purification of fungal lysates will be apparent to the skilled person. In one example, the germinated spores of the fungi are lysed. For example, the lysates are obtained by homogenizing germinated spores of fungi. As exemplified herein, following germination of the spores, the mycelial mat is washed with sterile water and then homogenized using 0.5 mm zirconia-silica beads in a mini-beadbeater-8 cell homogenizer. Fungal lysates are clarified by centrifugation and passed through 0.22 μm sterile filters.

Methods for measuring the protein content of fungal lysates will be apparent to the skilled person and include the bicinchoninic acid (BCA) protein assay kit.

In one example, the lysate is not contaminated with bacteria or fungi. In one example, the sterility of lysates is confirmed by the absence of bacterial or fungal growth after incubation for two weeks at 30° C. in liquid culture medium.

Antigen Presenting Cells

As discussed above, exemplary T cells are produced with antigen presenting cells exposed to water soluble lysates of *A. terreus* and *C. krusei*.

In one example, the antigen presenting cells are dendritic cells. For example, monocytic derived dendritic cells. Exemplary monocyte derived dendritic cells (MoDC) are isolated from peripheral blood mononuclear cells (PBMC), peripheral blood stem cells (PMSC) or hematopoietic progenitor cells (HPC).

In one example, PBMC are isolated from heparinised blood by gradient centrifugation over Ficoll-paque. In one example, the donors of peripheral blood are immunologically normal undergoing therapeutic venesection. In one example, 300-500 mL of peripheral blood is collected for isolation of PBMC. In one example, the PBMC are cryopreserved in 10% dimethylsulfoxide (DMSO) solution.

In one example, monocytes are isolated following mobilisation of stem cells by administration of granulocyte-colony stimulating factor (G-CSF). In one example, donors of stem cells are healthy individuals donating for allogeneic hematopoietic stem cell transplantation. In one example, the monocytes are freshly isolated. In another example, the PMSC or monocytes are cryopreserved in 10% DMSO solution.

In one example, monocytes are isolated following harvest of bone marrow. In one example, donors of bone marrow are healthy individuals donating for allogeneic hematopoietic stem cell transplantation. In one example, the bone marrow mononuclear cells are freshly isolated. In another example, the bone marrow mononuclear cells are cryopreserved in 10% DMSO solution.

In one example, HPC are isolated by washing in phosphate buffered saline containing 1% human albumin. In one example, the HPC are freshly isolated. In another example, the HPC are cryopreserved in 10% DMSO solution.

Exemplary MoDC are isolated from PBMC or HSC by adherence to plastic or by CD14+ magnetic nanoparticle separation, and differentiated into immature dendritic cells in CellGro™ DC medium for about 6 days. In one example, the medium is supplemented with 1000 U/mL granulocyte macrophage colony-stimulating factor (GM-CSF) and/or 1000 U/mL IL-4.

In one example, the antigen presenting cells are irradiated. For example, the antigen presenting cells are irradiated at 30 Gy.

In one example, the antigen presenting cells are pooled prior to use.

Testing for Activity

Methods for testing activity of the T cells e.g., fungal cross-reactivity, will be apparent to the skilled person based on the disclosure herein.

Testing for Lymphoproliferative Activity of Fungal Lysates

In one example, the lymphoproliferative activity of the fungal lysate is assessed. As exemplified herein, one method for assessing the activity of fungal lysates on lymphoid cells is using a $^3$H-thymidine incorporation assay. Such a process may involve the stimulation of PBMC ($2 \times 10^5$ cells/200 μl) with 10 μg/ml of individual fungal lysate. IL-2 (25 U/ml) may be used as positive control and lysate from K562 cells (10 μg/ml) may be used as an irrelevant control. The lymphoproliferative activity may be assessed by addition of one μCi of thymidine followed by overnight incubation at 37° C., lysing of cells and harvesting of the cellular material onto filter mats. $^3$H-thymidine incorporation can be assessed on a Microbeta™2 plate reader.

The reagents for determining lymphoproliferative activity are commercially available from Perkin Elmer.

Cell Phenotype Analysis

In one example, the T cells are phenotyped.

As exemplified herein, one method of phenotyping the T cells is staining the cells with fluorophore-conjugated antibodies to human CD3 (SK7), CD4 (RPA-T4), CD8 (SK1), CD19 (SJ25C1), CD14 (MφP9), CD56 (NCAM16.2), Vδ2TCR (B6), CD45RO (UCHL1), CD45RA (HI100), CD62L (Dreg56), CD25 (2A3), CD28 (L293), CD154 (TRAP1), CD161 (DX12) (all from BD; clones indicated in parentheses), Foxp3 (259D) (Biolegend) and CCR4 (205410) (R&D Systems).

In a further example, the T cell subsets can be defined by expression of molecules by flow cytometry. T cell subsets can be defined as: naïve $CD3^+CD45RA^+CD62L^+$, terminally differentiated effector ($T_{eff}$) $CD3^+CD45RA^+CD62L^-$, effector memory ($T_{em}$) $CD3^+CD45RA^-CD62L^-$, central memory ($T_{cm}$) $CD3^+CD45RA^-CD62L^+$ and regulatory T cells ($T_{reg}$) $CD4^+CD25^{hi}Foxp3^+$.

Carboxyflourescein Ester (CFSE) Proliferation Assay

In one example, the proliferative activity of the cultured T cells is assessed.

As exemplified herein, one method of assessing the proliferative activity of cultured T cells is to stain the cells with 1.5 μM carboxyfluorescein succinimidyl ester (CFSE) for 10 min at 37° C. then wash and co-culture the cells with autologous MoDC exposed with individual fungal lysate. The loss of CFSE fluorescence in cells after 7 days is then assessed by flow cytometry following co-staining with CD4 and CD8 antibodies.

Fungal Hyphal Damage Assay

In one example, the antifungal activity of the T cells is assessed.

As exemplified herein, one method of assessing the antifungal activity is using a calorimetric assay with 2,3-bis[2-methoxy-4-nitro-5-sulfophenyl]2H-tetrazolium-5-carboxyanilide sodium salt (XTT) and 2-methyl-1,4-napthoquinone (menadione). Such a process may involve germinating the fungal spores at 37° C. in 96-well microculture plates and incubating for a period of time. Exemplary incubation times include: *A. fumigatus* and *L. prolificans* 16-28 h, *A. terreus*, *C. albicans* and *C. krusei* 16-20 h. The hyphal masses are then washed twice in PBS by centrifuging at 15,000 g for 15 minutes in a plate centrifuge. PBMC, white blood cells (WBC) and fungus-specific T cells can then be added to appropriate wells at an effector to target ratio of 5:1 ($5 \times 10^4$ of each cell type). Following incubation at 37° C. for 2 hours, cells are lysed by washing twice in sterile water. The hyphal masses are resuspended in 200 μl sterile water and then 10 μl of XTT-menadione reagent is added to each well. The plate is vortexed gently then incubated at 37° C. for 2 hours. Following incubation, plates are centrifuged at 4,000 g for 10 minutes, the supernatant collected and the absorbance of the XTT reduction product (formazan) measured at 450 nm filter using a 620 nm reference on the Victor™ 3 plate reader. Absorbance may be standardized against unconverted XTT in wells containing only media and the XTT/menadione solution. Percent hyphal damage (HD) can be calculated as follows: % $HD=(1-X/C) \times 100$, where X is the absorbance of test well and C is the absorbance of the control wells with hyphae only Cytometric Bead Array In one example the levels of cytokines in supernatants of antigen-stimulated T cells is assessed.

As exemplified herein, one method of assessing the levels of cytokines in supernatants of antigen-stimulated T cells is using a cytometric bead array. Such a process may involve stimulating cultured T cells with unexposed control MoDC or MoDC exposed to a combination of one or more or all fungal lysates. The levels of TNFα, IFNγ, IL-2, regulated upon activation, normal T cell expressed and secreted (RANTES), monocyte chemoattractant protein (MCP)-1, macrophage inhibitory protein (MIP)-1β, IL-4, IL-8 and IL-17 in the cell-free supernatants can be measured after 5 hours of stimulation by cytometric bead array.

A kit for performing the cytometric bead array is commercially available from BD.

T Cell Compositions

The composition of the present disclosure is useful for parenteral administration for prophylactic or for therapeutic treatment of, e.g., superficial or invasive fungal disease (and, optionally, a viral infection).

In one example, the T cells are isolated following contacting with a population of cells comprising antigen presenting cells which have been previously exposed to a water soluble lysate(s) of a fungus and/or to a viral antigen(s), and formulating the population of cells into a pharmaceutically acceptable carrier.

In one example, the composition comprises isolated T cells reactive with a water soluble fungal lysate.

In one example, the composition comprises isolated T cells reactive with a viral antigen. For example, the viral antigen comprises overlapping peptides from viral proteins, a lysate of virally infected cells, cells genetically engineered with retrovirus, lentivirus or other vectors to express a viral protein.

In one example, the composition comprises isolated T cells reactive with a water soluble fungal lysate and isolated T cells reactive with a viral antigen.

In one example, the T cells are reactive with one or more viruses selected from the group consisting of CMV, EBV, AdV, VZV, influenza, BK virus, JC virus, RSV, *parainfluenzae*, rhinovirus, human metapneumovirus, HSV 1, HSV II, HHV6, HHV8, hepatitis A virus, hepatitis B virus, hepatitis C virus, hepatitis E virus, rotavirus, papillomavirus and parvovirus.

In one example, the composition comprises T cell products that meet the following release criteria:

Greater than 50% post thaw viability;
Less than 2% B cells and monocytes;
Negative for bacterial and fungal contamination at 5 days;
Negative for *Mycoplasma* contamination;
No evidence of alloreactivity defined as <10% specific cytotoxicity against recipient derived PHA blasts at a ratio of 20:1 effector cells to target cells in a standard $^{51}$CR assay;
Non-reactive for infectious disease markers.

In one example, the cells are autologous to the subject receiving the treatment. In one example, the cells are non-autologous to the subject.

Formulation of the composition to be administered will vary according to the route of administration and formulation (e.g., solution, emulsion) selected. An appropriate pharmaceutical composition comprising the composition of the present disclosure to be administered can be prepared in a physiologically acceptable carrier. A mixture of compositions can also be used. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, Remington's Pharmaceutical Science, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate.

The optimum concentration of cell populations in the chosen medium can be determined empirically, according to procedures well known to the skilled artisan, and will depend on the ultimate pharmaceutical formulation desired.

Dosage and Administration

The dosage ranges for the administration of the composition of the disclosure are those large enough to produce the desired effect. For example, the composition comprises an amount sufficient to confer a therapeutic or protective immune response in the subject.

The dosage should not be so large as to cause adverse side effects, such as hyper viscosity syndromes, pulmonary edema, congestive heart failure, and the like. Generally, the dosage will vary with the age, condition, sex and extent of the disease in the subject and can be determined by one of skill in the art. The dosage can be adjusted by the individual physician in the event of any complication. Dosage can vary from about $1\times10^3$ cells/kg to about $1\times10^{10}$ cells/kg. For example about $1\times10^3$ cell/kg to about $1\times10^4$ cells/kg, or about $1\times10^4$ cell/kg to about $1\times10^5$, or about $1\times10^5$ cell/kg to about $1\times10^6$, or about $1\times10^6$ cell/kg to about $1\times10^7$, or about $1\times10^7$ cell/kg to about $1\times10^8$, or about $1\times10^8$ cell/kg to about $1\times10^9$, or about $1\times10^9$ cell/kg to about $1\times10^{10}$. Dosage can vary from about $1\times10^5$ cells/m$^2$ to about $1\times10^{10}$ cells/m$^2$. For example, about $1\times10^5$ cells/m$^2$ to about $1\times10^6$ cells/m$^2$, or about $1\times10^6$ cells/m$^2$ to about $1\times10^7$ cells/m$^2$, or about $1\times10^7$ cells/m$^2$ to about $1\times10^8$ cells/m$^2$, or about $1\times10^8$ cells/m$^2$ to about $1\times10^9$ cells/m$^2$, or about $1\times10^9$ cells/m$^2$ to about $1\times10^{10}$ cells/m$^2$. For example, about $1\times10^7$ cells/m$^2$, or about $2\times10^7$ cells/m$^2$, or about $3\times10^7$ cells/m$^2$, or about $4\times10^7$ cells/m$^2$ or about $5\times10^7$ cells/m$^2$. In one example, the dosage may be administered in one or more dose administrations. In one example, the dosage can be repeated at least once. For example, the dosage is repeated at intervals depending on the immune state of the subject and the response to the previous infusion. In this regard, the repeat dosage(s) need not be the same as previous dosage(s), e.g., it could be increased or decreased.

In one example, the composition is administered intravenously.

In the case of a subject that is not adequately responding to treatment, multiple doses may be administered. Alternatively, or in addition, increasing doses may be administered.

Conditions to be Treated

In one example, administration of the T cell population to a subject confers a therapeutic immune response against fungi.

In one example, administration of the T cell population to a subject confers a protective immune response against fungi.

In one example, the subject is suffering from a disease or condition. For example, the disease or condition is a cancer, such as a blood or bone marrow cancer, for example the cancer includes multiple myeloma, leukemia, lymphoma, neuroblastoma, Ewing sarcoma, myelodysplastic syndromes and gliomas. In another example, the disease or condition is a non-malignant condition, for example thalassemia, aplastic anemia, fanconi anemia and immune deficiency syndromes. In a further example, the condition or disease is associated with infection or graft-versus host disease.

In one example, the subject is undergoing treatment for a disease or condition. In one example, the subject is about to commence or has completed treatment for a disease or condition. In one example, the treatment is chemotherapy, hematopoietic stem cell transplantation or immunoablation. For example, the subject is undergoing or about to commence or has completed chemotherapy and/or hematopoietic stem cell transplantation and/or immunoablation therapy.

In one example, the subject is about to receive or has received transplantation of a solid organ such as a kidney, liver, pancreas, pancreatic islets, heart, lungs, small bowel or other solid organ.

In one example, the subject is receiving or has received immunosuppressive drug treatment or antibody treatment or soluble receptor treatment or another immunomodulating treatment for a disease such as, but not limited to, inflammatory bowel disease, rheumatoid arthritis, multiple sclerosis, hepatitis, glomerulonephritis and kidney failure, cancer, lymphoma, leukemia, myelodysplasia, myeloma.

In one example, the subject has inherited or been born with a deficiency of the immune system such as, but not limited to, severe combined immune deficiency, common variable immunodeficiency, alymphocytosis, Wiskott Aldrich syndrome, ataxia telangiectasia, di George syndrome, leucocyte adhesion defects, immunoglobulin deficiency.

In one example, the subject has an acquired immunodeficiency through infection with the human immunodeficiency virus or another pathogenic organism that has led to incompetence of the immune system.

In one example, the subject is suffering from chronic relapsing fungal infections such as, but not limited to, chronic or relapsing oral or vulvovaginal candidiasis, chronic or relapsing fungal skin infection, chronic or relapsing fungal nail infections, chronic or relapsing fungal bronchial infections, chronic or relapsing fungal sinus infections, chronic or relapsing fungal myocardial infections, chronic or relapsing fungal cerebral infections, chronic or relapsing fungal bone infections, chronic or relapsing fungal liver infections, chronic or relapsing fungal kidney or bladder infection.

Phenotyping of Cells for Use in Therapy and Banking

In one example, the cells of the present disclosure are HLA-allele phenotyped. For example, the cells are partially HLA-allele phenotyped.

In one example, the cells have alleles selected from major HLA, such as any Class I, II or III HLA, minor HLA, and non-polymorphic alleles, such as any member of the CD1 family members.

Major HLA alleles may more specifically be selected from any class I HLA such as HLA-A1, HLA-A2, HLA-A3, HLA-A24, HLA-A11, HLA-A28, HLA-A29, HLA-A32, HLA-B15, HLA-B5, HLA-B7, HLA-B8, HLA-B12, HLA-B14, HLA-B18, HLA-B35, HLA-B40, HLA-C group 1, HLA-C group 2 for example, any class II HLA-DPB9, HLA-DPB11, HLA-DPB35, HLA-DPB55, HLA-DPB56, HLA-DPB69 HLA-DPB84 HLA-DPB 87, HLA-DRB1, HLA-DQA1, HLA-DQB1, or any class III HLA. The knowledge of a HLA phenotype can facilitate subsequent selection of cells for the preparation of the composition of the present disclosure.

In one example, at least one class II HLA is phenotyped. For example, at least one of HLA-DR, HLA-DP or HLA-DQ is phenotyped.

In one example, at least one HLA-allele in the cells of the present disclosure is matched to at least one HLA-allele in the subject to which the composition is administered. For example, at least one class II HLA is matched. For example, at least one of HLA-DR, HLA-DP and HLA-DQ is matched.

In one example, the HLA allele is HLA-DR. For example, the phenotype of HLA-DR in the cells of the present disclosure is matched to an HLA-DR allele in the subjection to which the composition is administered. In one example, the method of treating a subject comprises determining an HLA allele in the subject, matching the HLA allele to an HLA allele in T cells in a composition in the bank and administering to the subject a composition comprising T cells having the same HLA allele as that in the subject.

In one example, the method additionally comprises testing the composition for anti-fungal activity. For example, the method comprises testing the composition for activity against a fungus with which a subject is infected.

Banking of T Cells

In one example, a plurality of T cell compositions are in a bank.

The cells for use in the present disclosure may be "banked" for future use, at a cell bank or depository or storage facility, or any place where such as cells are kept cryopreserved, e.g., in liquid nitrogen, for safekeeping. Furthermore, appropriate computer systems can be used for data processing, to maintain records relating to donor information and to ensure rapid and efficient retrieval of cells from the storage repositories.

In one example, each of the storage containers (e.g., bags or tubes) can be tagged with positive identification based on a distinctive property associated with the donor, lines or cell type, prior to storing in a bank according to the disclosure. For example, DNA genetic fingerprint and HLA typing may be used with secured identification mechanism such as acceptable methods using microchips, magnetic strip, and/or bar code labels. This identification step may be included in the banking process.

In one example, at least one of the HLA alleles in the T cells in each composition in the bank has been identified. In one example, the HLA is a HLA-DR allele.

At the time of use, only the required storage unit is retrieved, the number of units necessary to fulfil a desired dosage being selectable. Certain diseases may require cell therapy that includes a series of repeated treatments. The population of cells may be extracted from the bank and increased by cellular expansion before preparation of the pharmaceutical composition and administration to the subject.

Suitable cells for use in the preparation of the composition of the present disclosure may be obtained from existing cell banks, or may be directly collected from one or more donor subjects and later banked. In one example, cells are collected from healthy subjects. For example, cells from tissues that are non-essential to the subject may also be appropriate as they reduce the risk of induction of autoimmune disease.

Standards for donor selection may include one or more of the following considerations prior to collection, such as (a) absence of specific disease; (b) specific or general diseases; (c) parameters of the donor relating to certain diseases, for example a certain age, certain physical conditions and/or symptoms, with respect to certain specific diseases, with respect to certain prior treatment history and/or preventive treatment, etc.; (d) whether the donor fits into one or more established statistical and/or demographic models or profiles (e.g., statistically unlikely to acquire certain diseases); and (e) whether the donor is in a certain acceptable health condition as perceived based on prevailing medical practices, etc.

In one example, the cells are collected by apheresis from donor's peripheral blood, processed (to optimise the quantity and quality of the collected cells) and, optionally cryogenically preserved or maintained in culture under suitable conditions.

In one example, the donor is a stem cell donor. For example, the cells are collected by apheresis as part of the stem cell donation. In one example, the cells are collected after administration of G-CSF to the donor alone or in combination with chemotherapy or a stem cell mobilising agent. In one example, the cells are collected by bone marrow harvest.

In one example, the cells are collected by apheresis from the donor's peripheral blood or from the bone marrow by marrow harvest and are used for the preparation of the composition if the number of cells collected exceeds the number required for the purposes of stem cell transplantation. For example, the cells collected for the preparation of the composition are in excess of the cells required for stem cell transplantation.

The collected cells can be aliquoted into defined dosage fractions. The cells may be stored under any appropriate conditions, such as in culture or in a cryopreserved state. Methods of cell stored will be apparent to the skilled person. For example, cryopreservation of cells can be achieved using a variety of cryoprotecting agents, such as DMSO.

In one example, the cells may be cryopreserved at different stages. For example, the cells may be cryopreserved as PBMC, isolated monocytes, dendritic cells and after about 1 to 2 weeks culture as fungus specific T cells.

As exemplified herein T cells are cryopreserved for adoptive T cell transfer. For example, a freezing mix containing 40% saline, 40% Albumex20 and 20% DMSO is prepared. The saline is added to the DMSO and chilled before adding the Albumex20. The freezing mix is kept chilled until required.

The cells for cryopreservation are resuspended, pooled and mixed thoroughly. The cells are counted using a haemocytometer and the cell concentration and total cell viability is determined.

The cells are spun at 1400 rpm for 5 mins and 10 mls of the supernatant is removed for sterility and *mycoplasma* testing. The remaining supernatant is discarded.

The cells are washed with up to 200 ml of 0.9% saline supplemented with Albumex20 and spun at 1400 rpm for 5 mins.

The cells are resuspended in 0.9% saline at a concentration of $2 \times 10^7$ cells/ml.

For cryopreserving the T cells the maximum volume of cells to be added per bad is to be calculated using the formula: Maximum volume per bag (mL)=Max number of cells required per bag/1×10⁷ per ml.

The number of bags and quality assurance samples to be cryopreserved is determined. An equal volume of freezing mix is added to the T lymphocyte suspension and mixed. The required volume of cells is transferred into cryopreservation bags and/or vials. The bags and vials are immediately placed into pre-cooled rate controlled freezers to begin cryopreservation.

EXAMPLES

Example 1—Isolation of Fungal Antigens and PBMCs

Isolation of Fungal Antigens

Pure strains of fungi were isolated from the environment (*Aspergillus fumigatus* strain WMI-008, *A. terreus* WMI-026 and *Fusarium oxysporum* WMI-011), from clinical specimens (*Fusarium solani, Rhizopus oryzae, Lomentospora prolificans, Candida albicans, C. krusei* and *C. glabrata*) or from ATCC (*A. flavus* strain ATCC-204304).

Fungi were sub-cultured on potato dextrose agar plates for 3-7 days. Spores were removed by washing and separated from hyphal fragments by filtration (40 μm or 60 μm pore filters). Spores were germinated in potato dextrose medium for 16-72 hours at 25-37° C. with agitation at 200 rpm. The mycelial mat was washed with sterile water and then homogenized. Lysates were clarified by centrifugation and passed through 0.22 μm sterile filters. Protein content was measured.

Sterility of lysates was confirmed by the absence of bacterial or fungal growth after incubation for two weeks at 30° C. in liquid culture medium. Lysates were stored at −80° C. To use as negative control, water-soluble lysate was prepared from K562 cells using the same homogenization procedure used for the preparation of fungal lysates.

Isolation of PBMC and HPC

Peripheral blood mononuclear cells (PBMC) were isolated from heparinised blood by gradient centrifugation over Ficoll-paque.

Peripheral blood stem cells (PMSC) were isolated following mobilisation of stem cells by administration of granulocyte-colony stimulating factor (G-CSF). Hematopoietic progenitor cells (HPC) were isolated by washing in phosphate buffered saline containing 1% human albumin.

Example 2—Lymphoproliferative Activity of Fungal Lysates

The activity of lysates on lymphoid cells was confirmed using a ³H-thymidine incorporation assay. PBMC ($2\times10^5$ cells/200 μl) were stimulated with 10 μg/ml of individual fungal lysate. IL-2 (25 U/ml) was used as positive control and lysate from K562 cells (10 μg/ml) was used as an irrelevant control. One μCi of thymidine was added on day 7 and incubated overnight at 37° C. Cells were lysed by washing with water and cellular material harvested onto filter mats. ³H-thymidine incorporation was analysed on the Microbeta2 plate reader. Means of quadruplicates were calculated and expressed relative to numbers obtained in unstimulated conditions.

Mean fold increases in ³H-thymidine uptake relative to control at the end of 7 days varied from 10.7 (range 2.1-23.1) for *C. krusei* to 58.4 (15.1-150) for *A. terreus* (FIG. 1). The observed responses were specific, as lysate from K562 cells that was generated similarly, did not induce proliferation in T cells.

Example 3—Frequency of Fungus Antigen-Specific Cells in Peripheral Blood

The numbers of fungus-specific TNFα and IFNγ spot forming cells in the starting PBMC population were quantified by ELISPOT analyses. Sterile multiscreen 96-well filtration plates were coated overnight with 5 μg/ml of IFNγ or TNFα capture antibody then blocked with complete AIM-V™ medium containing 10% pooled human AB serum. PBMC ($0.5\text{-}2\times10^6$ per well) were stimulated in the antibody-coated plates overnight with 10 μg/ml of each fungal lysate or 5 μg/ml phytohemagglutinin as a positive control. Unstimulated PBMC served as negative control.

Cells were removed by washing and spots developed by sequential addition of biotinylated detection antibody, 0.1% extravidin-alkaline phosphatase and substrate Sigma Fast solution. Spots were counted and normalized to the number of spots per $1\times10^6$ PBMC for each condition. Means of triplicates were calculated and background from control unstimulated conditions subtracted from each test condition. A positive response was greater than 2 times the number of spots above control for each donor.

IFNγ responses were observed in 8 of 10 donors (Table 1) towards *C. albicans*, 7 donors towards *A. terreus, F. oxysporum* and *L. prolificans*, 6 donors towards *A. fumigatus, A. flavus* and *F. solani*, and 3 donors towards *C. krusei* and *R. oryzae*. TNFα responses were observed in 7 of 10 donors towards *A. fumigatus*, and *C. abicans*, 6 donors towards *A. flavus*, 5 donors towards *F. solani, F. oxysporum* and *L. prolificans*, 3 donors towards *A. terreus*, 2 donors towards *C. krusei* and 1 donor towards *R. oryzae*.

The percentage of T cells in the starting PBMC that were specific to each fungus was determined by measuring TNFα expression by flow cytometry in 3 normal donors. In all cases, the percentages of CD4⁺ cells that expressed TNFα were less than 0.05%.

TABLE 1

Numbers of fungus-specific IFNγ and TNFα spot forming cells in the peripheral blood of healthy donors

| | Median SFC per $1 \times 10^6$ cells (range); N | |
|---|---|---|
| | IFNγ | TNFα |
| *A. fumigatus* | 9 (0-274); 6 | 404 (0-2290); 7 |
| *A. flavus* | 19 (0-533); 6 | 390 (0-1863); 6 |
| *A. terreus* | 18 (0-190); 7 | 146 (0-816); 3 |
| *C. albicans* | 36 (0-147); 8 | 184 (0-936); 7 |
| *C. krusei* | 0 (0-274); 3 | 0 (0-889); 2 |
| *F. solani* | 29 (0-353); 6 | 129 (0-940); 5 |
| *F. oxysporum* | 30 (0-336); 7 | 117 (0-1742); 5 |
| *R. oryzae* | 6 (0-26); 3 | 19 (0-288); 1 |
| *L. prolificans* | 6 (0-97); 7 | 129 (0-1832); 5 |

Abbreviation:
SFC—spot forming cells;
N—number of donors out of 10 where a positive response was observed as defined by greater than 2 times the number of spots above control for each donor.

Example 4—Generation of Fungus Specific T Cell Cultures

Isolation of Monocyte-Derived Dendritic Cells

Monocytes were isolated from PBMC or HPC by adherence to plastic or by CD14⁺ magnetic nanoparticle separation. Monocytes were differentiated into immature dendritic cells (DC) in CellGro™ DC medium containing 1000 U/mL granulocyte macrophage colony-stimulating factor (GM-CSF) and 1000 U/mL IL-4 for 6 days.

MoDC were exposed overnight with 10 μg/mL fungal lysate and matured with 200 U/ml TNF-α overnight. Exposed MoDC were harvested, washed and resuspended in AIM V lymphocyte medium and irradiated at 30 Gy.

Culture of T Cells Specific for Individual Fungus

PBMC were stimulated with autologous MoDC exposed to individual fungal lysate at MoDC:PBMC ratios of 1:10 in complete AIM-V™ medium. A second stimulation was performed on day 7. Cells were expanded with addition of 20 U/mL IL-2, 10 ng/mL IL-15 and 10 ng/mL IL-7 from day 7 onwards, with the concentration of IL-2 increased to 50 U/mL from day 14 until day 21.

Figure 2A:
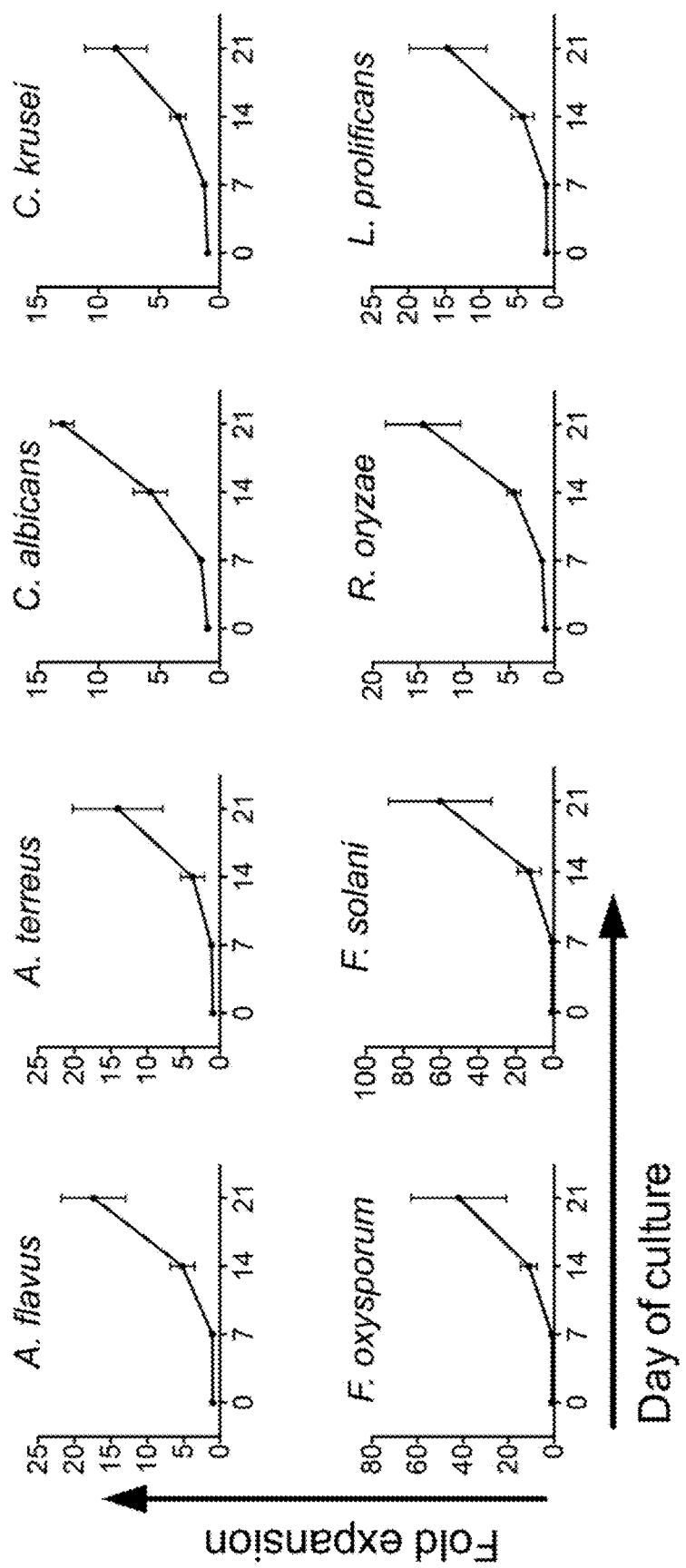
FIG. 2A-FIG. 2B are graphical characterisations of individual fungal T cell cultures.

Four T cell cultures specific for each one of the fungus were established (Table 2). The fold increases in cell numbers over the 21 day culture period varied from 8.6 for *C. krusei* to 60.6 for *F. solani* (FIG. 2a). All fungal T cell cultures generated greater than 70% CD4$^+$ cells, except in the case of T cell cultures stimulated with *C. krusei* and *F. solani* lysates which generated 59.0±31.7 and 63.0±10.8% CD4$^+$ cells and 18.5±13.5% and 29.6±9.3% CD8$^+$ cells respectively. At the completion of culture, the presence of fungus-specific T cells was assessed by measuring intracellular expression of the Th1 cytokines, IFNγ, TNFα and IL-2 following re-stimulation with the same fungal lysate used to originate the T cell culture.

Figure 2B:
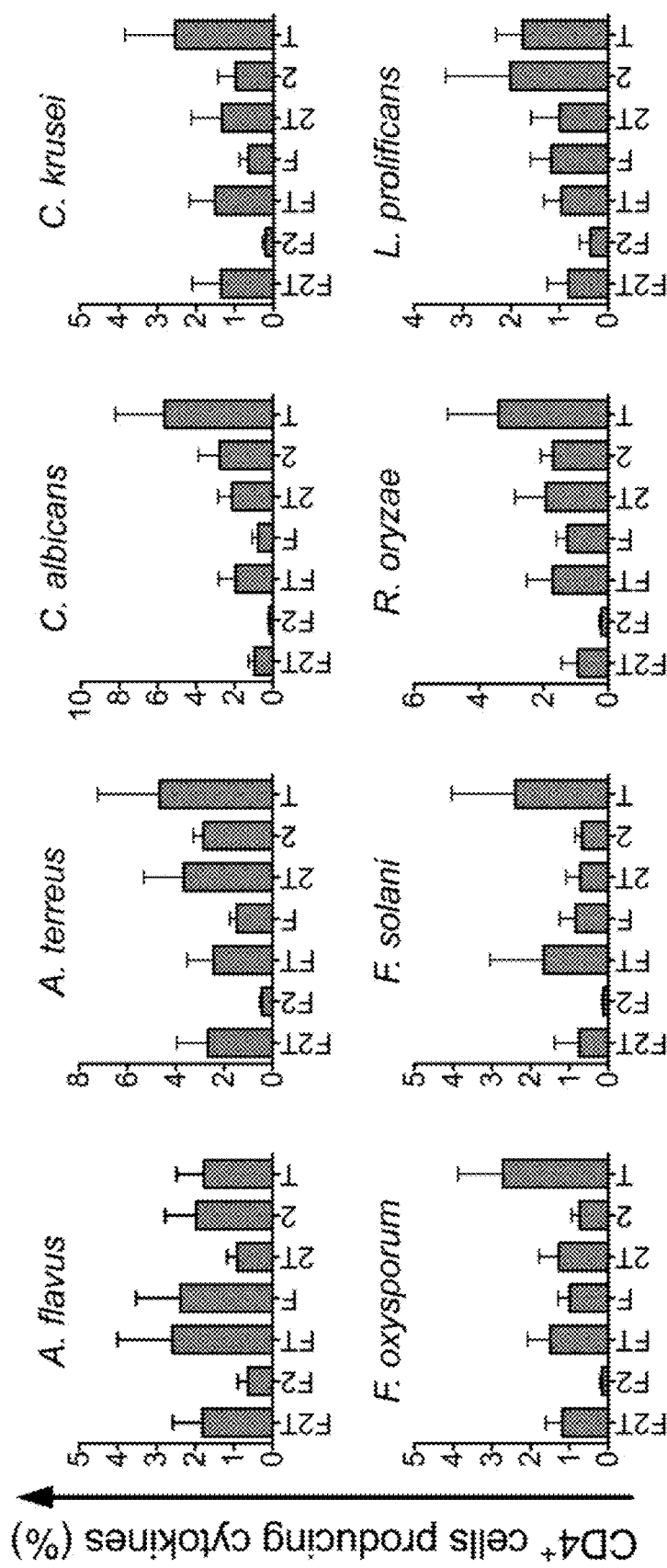

Fungus-specific CD4$^+$ cells were present in all cultures. The percentages of CD4$^+$ cells that responded by production of at least one Th1 cytokine (TNFα, IFNγ or IL-2 or any combination) varied from 7.1±4.3% for *F. solani* to 18.3±6.7% for *A. terreus*. The percentage of CD4$^+$ cells that expressed intracellular TNFα following stimulation varied from 4.4±3.9% for *L. prolificans* to 13.2±12.8% for *A. terreus*. The majority of the responding CD4 cells produced one cytokine, however 2.2-6.6% and 0.7-2.7% of polyfunctional double and triple cytokine-producing cells respectively were present in all cultures (FIG. 2b). TNFα was the predominant Th1 cytokine produced except for *A. flavus*-specific T cells, which most commonly produced IFNγ alone or in combination with TNFα, and *L. prolificans*-specific T cells which predominantly produced IL-2. Two *A. terreus*, two *F. oxysporum*, three *F. solani* and two *R. oryzae* cultures also demonstrated positive CD8 responses (0.5-3.2% of CD8 cells expressing Th1 cytokines).

Cross-Reactivity of Cultured T Cells with Other Fungal Antigens

The responses of cultures originated with each lysate to other fungi were assessed. Since the fungus-specific CD4 responses observed in starting PBMC were less than 0.05%, TNFα production of greater than a log higher (i.e., greater than 0.5%) was used to qualify as a positive response in the expanded T cell cultures.

All *A. terreus*, *F. oxysporum* and *L. prolificans* T cell cultures showed cross-reactivity with one another and with lysates from *A. fumigatus*, *A. flavus* and *F. solani* (Table 3). All *C. krusei* T cell cultures cross-reacted with lysate derived from *C. albicans*, while some cross-reacted with *Aspergillus* and *Fusarium* species. Cross-reactivity with *R. oryzae* was only observed in a subset of the T cell cultures (2 of *F. oxysporum*, 2 of *L. prolificans* and one each of *A. flavus*, *A. terreus* and *C. krusei* specific T cell cultures).

*A. terreus*, *R. oryzae* and *C. krusei* were selected as a 3-antigen combination to generate panfungal T cell products with broad cross-reactivity towards all fungi.

TABLE 2

Characteristics of T cells generated from cultures stimulated with individual fungal lysates.

|  | Mean fold increase in cell number (range) | % T cells at end of culture | % CD8 cells at end of culture | % CD4 cells at end of culture | % CD4$^+$ cells producing any Th1 cytokine in response to restimulation | % CD4$^+$ cells producing TNFα in response to restimulation |
|---|---|---|---|---|---|---|
| *A. flavus* | 17.4 (9.7-27.6) | 91.9 ± 9.3 | 8.0 ± 2.1 | 81.3 ± 8.9 | 12.1 ± 4.8 | 6.8 ± 5.5 |
| *A. terreus* | 14.1 (2.6-31.3) | 96.6 ± 3.4 | 7.7 ± 5.1 | 85.7 ± 8.8 | 18.3 ± 6.7 | 13.2 ± 12.8 |
| *C. albicans* | 13.0 (11.5-15.6) | 92.8 ± 6.7 | 4.9 ± 2.1 | 84.2 ± 10.1 | 14.5 ± 3.5 | 10.5 ± 8.5 |
| *C. krusei* | 8.6 (3.0-14.2) | 85.0 ± 25.7 | 18.5 ± 13.5 | 59.0 ± 31.7 | 8.6 ± 4.1 | 6.4 ± 6.8 |
| *F. oxysporum* | 41.9 (4.6-98.3) | 87.6 ± 19.7 | 6.7 ± 5.5 | 74.7 ± 32.6 | 8.6 ± 1.6 | 6.4 ± 3.8 |
| *F. solani* | 60.6 (2.3-109.6) | 96.1 ± 2.8 | 29.6 ± 9.3 | 63.0 ± 10.8 | 7.1 ± 4.3 | 5.2 ± 7.8 |
| *R. oryzae* | 14.5 (7.3-25.2) | 96.1 ± 3.8 | 4.6 ± 3.1 | 88.2 ± 7.2 | 11.1 ± 3.1 | 7.6 ± 6.4 |
| *L. prolificans* | 14.6 (5.6-28.2) | 96.0 ± 2.3 | 9.5 ± 1.6 | 81.3 ± 7.9 | 8.1 ± 3.8 | 4.4 ± 3.9 |

TABLE 3

Cross-reactivity analyses of fungal T cell cultures with other fungal antigens

|  |  | Cross-reactivity with | | | | | | | | |
|---|---|---|---|---|---|---|---|---|---|---|
|  |  | *A. fumigatus* | *A. flavus* | *A. terreus* | *C. albicans* | *C. krusei* | *F. oxysporum* | *F. solani* | *R. oryzae* | *L. prolificans* |
| T cell culture expanded with | *A. fumigatus* | 3 | 3 | 1 | 2 | 0 | 0 | 0 | NT | NT |
|  | *A. flavus* | 4* | 4* | 4* | 1 | 0 | 4* | 3 | 1 | 3 |
|  | *A. terreus* | 4* | 4* | 4* | 1 | 1 | 4* | 4* | 1 | 4* |
|  | *C. albicans* | 1 | 2 | 2 | 4* | 3 | 2 | 1 | 0 | 1 |
|  | *C. krusei* | 2 | 2 | 4* | 4* | 4* | 2 | 2 | 1 | 2 |
|  | *F. oxysporum* | 4* | 4* | 4* | 1 | 1 | 4* | 4* | 2 | 4* |
|  | *F. solani* | 2 | 2 | 2 | 1 | 1 | 2 | 4* | 0 | 2 |
|  | *R. oryzae* | 3 | 3 | 4* | 2 | 2 | 4* | 2 | 4* | 2 |
|  | *L. prolificans* | 4* | 4* | 4* | 0 | 0 | 4* | 4* | 2 | 4* |

The numbers indicate the number of cultures out of 4 where a positive response was observed, except in the case of *A fumigatus* where only 3 cultures were assessed.
*indicates cross-reactivity was observed in all cultures.
NT—not tested.

Example 5—Panfungal T Cell Culture Analysis

Generation of Panfungal T Cell Cultures

Eight cultures were established from unmobilized peripheral blood and three from G-CSF mobilized peripheral blood stem cell harvests using the *A. terreus, R. oryzae* and *C. krusei* lysate combination (10 µg/ml each) for antigen stimulation. Four PBMC cultures were generated without enrichment of antigen-specific cells and four with enrichment using TNF-α capture to isolate fungus-specific cells on day 7 of culture (Table 4).

Cells were stained with fluorophore-conjugated antibodies to human CD3 (SK7), CD4 (RPA-T4), CD8 (SK1), CD19 (SJ25C1), CD14 (MφP9), CD56 (NCAM16.2), Vδ2TCR (B6), CD45RO (UCHL1), CD45RA (HI100), CD62L (Dreg56), CD25 (2A3), CD28 (L293), CD154 (TRAP1), CD161 (DX12), Foxp3 (259D) and CCR4 (205410). Expression of molecules was assessed by flow cytometry. T cell subsets were defined as: naïve $CD3^+CD45RA^+CD62L^+$, terminally differentiated effector ($T_{eff}$) $CD3^+CD45RA^+CD62L^-$, effector memory ($T_{em}$) $CD3^+CD45RA^-CD62L^-$, central memory ($T_{cm}$) $CD3^+CD45RA^-CD62L^+$ and regulatory T cells ($T_{reg}$) $CD4^+CD25^{hi}Foxp3^+$.

All but one culture generated >89% T cells. T cells predominantly expressed the $T_{eff}$ and $T_{em}$ phenotypes and a minority also expressed the chemokine receptor CCR4 and the activation marker CD154 on their surface. In all cultures, the percentage of $T_{reg}$ cells was less than 6%.

In cultures generated from PBMCs without enrichment, the mean fold increase in cell numbers after 21 days was 10.6 fold (range 8.5-12.7) and the mean number of fungus reactive T cells at the end of culture in the three cultures assessed was $12.5\pm4.9\times10^6$ (Table 5). In the four cultures where antigen-specific cells were enriched on Day 7 using TNFα cytokine capture, the mean fold increase in total cell numbers after 21 days relative to starting cell numbers was 3.4 fold (range 0.7-9.8, n=4) and the total number of fungus reactive T cells at the end of culture were $3.0\pm3.9\times10^6$.

In the three cultures generated from PBSC without enrichment, the mean fold increase in cell numbers after 21 days of culture was 12.1 (range 8.7-15.0, n=3) and the total number of fungus reactive T cells at the end of culture was $19.1\pm9.6\times10^6$. The use of stem cell products resulted in the highest yield of fungus-specific cells, generating a mean of $19.1\pm9.6\times10^6$ fungus-specific $CD4^+$ cells after 21 days from a mean starting cell number of $12.0\pm4.0\times10^6$ (Table 5).

Figure 3A:
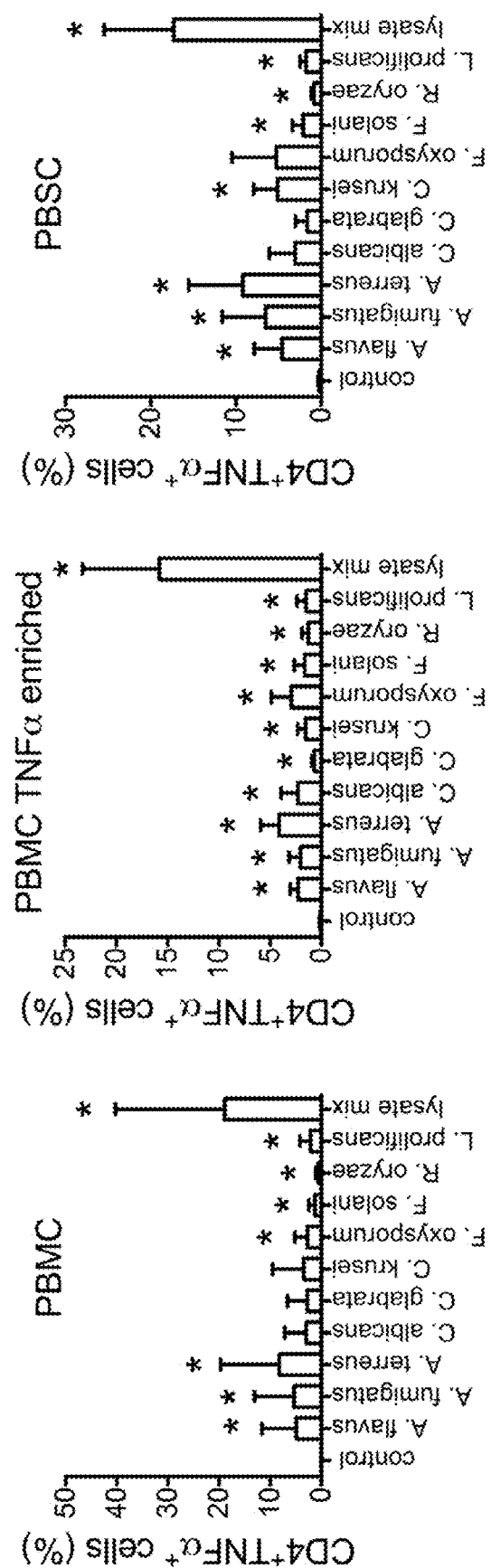
FIG. 3A-FIG. 3B are graphical characterisations of panfungal T cell products.

The specificity of panfungal T cell products was assessed by determining Th1 cytokine response to individual fungal lysates. The total percentage of fungus-reactive CD4 cells were $14.2\pm19.8$, $15.7\pm7.4$ and $17.0\pm8.1$ in cultures generated from PBMC, TNFα enriched PBMC and PBSC respectively (FIG. 3a). The cultured T cells demonstrated specificity towards multiple fungi. Fungus-specific IFNγ and IL-2 production by CD4 cells was also observed. The CD8 responses to individual lysates varied from 0 to 3% of cells expressing any Th1 cytokine except in one culture where up to 38% of CD8 cells expressed IL-2 in response to most fungal antigens. No intracellular Th1 cytokine production was observed when the cultured cells were stimulated with the irrelevant K562 lysate (n=4).

Proliferation of Panfungal T Cells Following Antigen Rechallenge

Figure 3B:
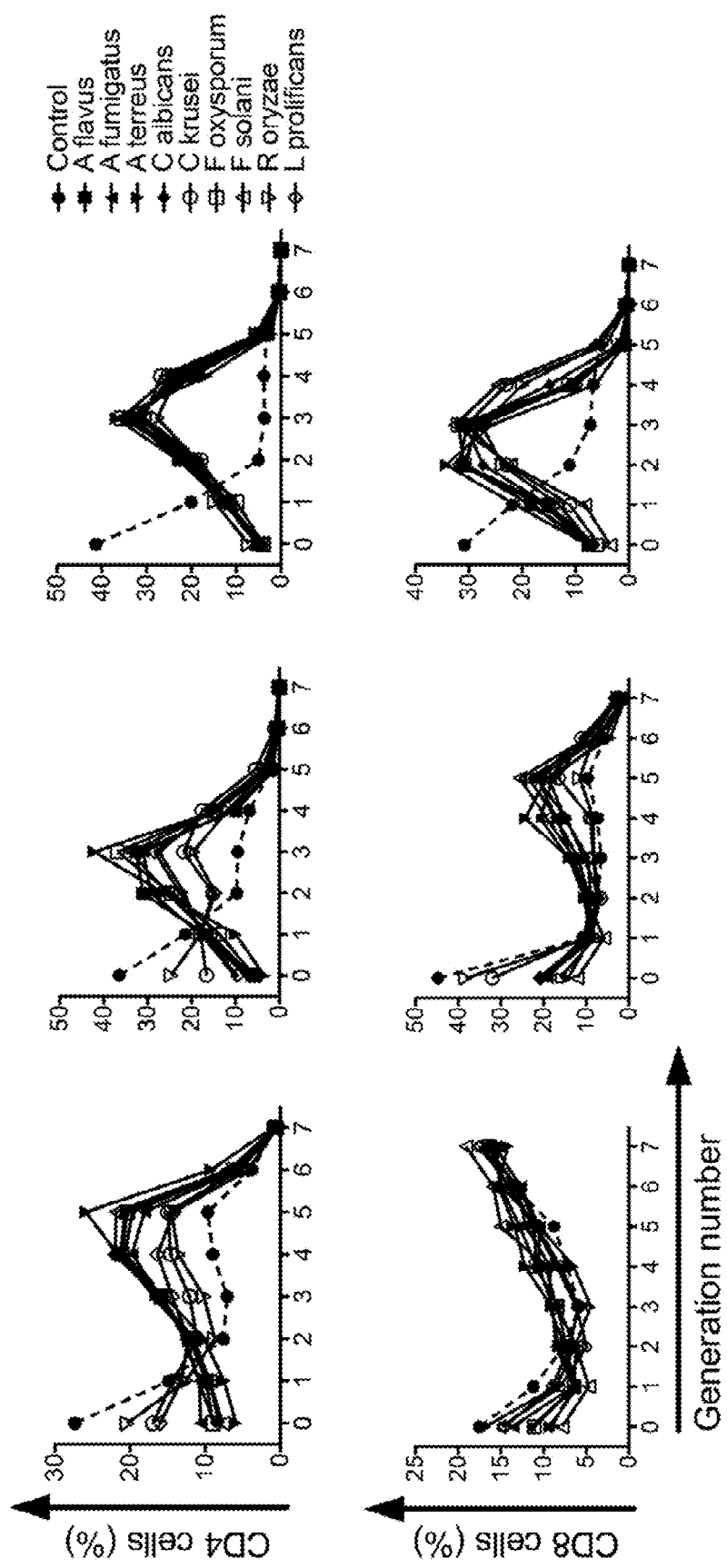

The capacity of cultured T cells to proliferate in response to stimulation with individual fungal lysates was assessed. Proliferation of $CD4^+$ cells in response to each fungal lysate was observed in all 3 cultures assessed and of $CD8^+$ cells in two of three cultures (FIG. 3b).

TABLE 4

Percentage expression of surface markers on multi-fungus responsive T cells expanded from PBMC and PBSC.

| | CD3 | CD4 | CD8 | CD56 | $T_n$ | $T_{eff}$ | $T_{em}$ |
|---|---|---|---|---|---|---|---|
| Peripheral Blood | | | | | | | |
| 1 | 94.3 | 88.5 | 4.4 | 4.3 | 11.9 | 41.3 | 88.8 |
| 2 | 90 | 83.8 | 4.7 | 7.5 | 5.5 | 67.4 | 70.2 |
| 3 | 94.2 | 81.9 | 11.1 | 5.7 | 2.4 | 49.8 | 84.8 |
| 4 | 95.7 | 34.6 | 43.3 | 23.9 | 6.5 | 49.3 | 92 |
| M | 93.6 ± 2.5 | 72.2 ± 25.5 | 15.9 ± 18.6 | 10.4 ± 9.1 | 6.6 ± 4.0 | 52.0 ± 11.0 | 84.0 ± 9.6 |
| Peripheral Blood- TNFα selected | | | | | | | |
| 5 | 28.1 | 26.8 | 0.7 | 61 | 19.3 | 35.9 | 88.2 |
| 6 | 98.1 | 31.3 | 58.7 | 1.1 | 19.7 | 38 | 72.3 |
| 7 | 90.6 | 79.0 | 6.4 | 8.7 | 10.4 | 48.9 | 85.6 |
| 8 | 89.5 | 64.0 | 21.8 | 6.5 | 4.4 | 36.9 | 81.5 |
| M | 76.6 ± 32.5 | 50.3 ± 25.3 | 21.9 ± 26.1 | 19.3 ± 28.0 | 13.5 ± 7.4 | 39.9 ± 6.0 | 81.9 ± 7.0 |
| Stem Cell Harvest | | | | | | | |
| 9 | 95.2 | 80.4 | 10.5 | 2.6 | 1.8 | 33.7 | 89.9 |
| 10 | 98.4 | 78.2 | 14.0 | 0.7 | 1.5 | 37.5 | 88.2 |
| 11 | 98.2 | 85.0 | 10.0 | 1.6 | 3.9 | 48.2 | 85.9 |
| M | 97.3 ± 1.8 | 81.2 ± 3.5 | 11.5 ± 2.2 | 1.6 ± 1.0 | 2.4 ± 1.3 | 39.8 ± 7.5 | 88.0 ± 2.0 |

| | $T_{cm}$ | $T_{reg}$ | CD3Vδ2TCR | CD3CD28 | CD4CCR4 | CD4CD154 |
|---|---|---|---|---|---|---|
| Peripheral Blood | | | | | | |
| 1 | 6.3 | 1.2 | 3.4 | 52.7 | 8.2 | 8.8 |
| 2 | 7.6 | 1.7 | 3.5 | 23.8 | 39.9 | 1.2 |
| 3 | 5.4 | 3 | 1.6 | 8.1 | 13.2 | 4.8 |
| 4 | 1.8 | 0.6 | 27.3 | 1.3 | 18.1 | 10.4 |
| M | 5.3 ± 2.5 | 1.6 ± 1.0 | 9.0 ± 12.3 | 21.5 ± 22.8 | 19.9 ± 14.0 | 6.3 ± 4.1 |

TABLE 4-continued

Percentage expression of surface markers on multi-fungus responsive T cells expanded from PBMC and PBSC.

| Peripheral Blood- TNFα selected | | | | | | |
|---|---|---|---|---|---|---|
| 5 | 6.7 | 0.1 | 5.3 | 40.9 | 11.8 | 11.5 |
| 6 | 10.8 | 1.6 | 2.2 | 5.5 | 40.2 | 8.4 |
| 7 | 5.8 | 0.3 | 7.2 | 19.7 | 21.7 | 18 |
| 8 | 11.5 | 5.7 | 2.6 | 0.2 | 20.2 | 11.4 |
| M | 8.7 ± 2.9 | 1.9 ± 2.6 | 4.3 ± 2.4 | 16.6 ± 18.2 | 23.5 ± 12.0 | 12.3 ± 4.0 |
| Stem Cell Harvest | | | | | | |
| 9 | 4.8 | 0.4 | 3.5 | 8.4 | 33.3 | 2.7 |
| 10 | 3.4 | 0.7 | 2.5 | 3.4 | 52.7 | 1 |
| 11 | 5.3 | 0.8 | 3.3 | 4.3 | 52.8 | 1.6 |
| M | 4.5 ± 1.0 | 0.6 ± 0.2 | 3.1 ± 0.5 | 5.4 ± 2.7 | 46.3 ± 11.2 | 1.8 ± 0.9 |

Abbreviations:
PBMC—peripheral blood mononuclear cells;
PBSC—peripheral blood stem cells;
$T_n$—naive T cells;
$T_{eff}$—terminally differentiated effector T cells,
$T_{em}$—effector memory T cells;
$T_{cm}$—central memory T cells,
$T_{reg}$—regulatory T cells;
Vδ2—Vδ2 gamma delta T cells,
M—mean.

TABLE 5

The expansion of multifungus T cell cultures generated from peripheral blood and stem cell harvests

| | Starting cell number ($\times 10^6$) | Cell number after TNFα enrichment ($\times 10^6$) | Fraction of selected cells (%) | Cell number after 21 d of culture ($\times 10^6$) | Expansion factor[a] | Number of fungus specific CD4⁻TNF⁺ cells ($\times 10^6$)[b] | Yield of fungus specific cells relative to starting cell number (%) |
|---|---|---|---|---|---|---|---|
| Peripheral Blood | | | | | | | |
| 1 | 14.1 | — | — | 179.6 | 12.7 | NT | — |
| 2 | 20 | — | — | 171.5 | 8.6 | 9.1 | 45.5 |
| 3 | 20 | — | — | 186 | 12.7 | 10.2 | 51 |
| 4 | 20 | — | — | 120 | 8.5 | 18.1 | 90.5 |
| M | 18.5 ± 3.0 | | | 164.3 ± 30.1 | 10.6 | 12.5 ± 4.9 | 62.3 ± 24.5 |
| Peripheral Blood- TNFα enriched | | | | | | | |
| 5 | 12.8 | 0.72 | 5.6 | 125 | 9.8 | 8.9 | 69.5 |
| 6 | 14.8 | 0.6 | 4.1 | 20.4 | 1.4 | 0.8 | 5.4 |
| 7 | 8.3 | 0.16 | 1.9 | 12.6 | 1.5 | 1.4 | 16.9 |
| 8 | 20 | 0.1 | 0.5 | 13.8 | 0.7 | 0.9 | 4.5 |
| M | 14.0 ± 4.9 | 0.4 ± 0.3 | 3.0 ± 2.3 | 43.0 ± 54.8 | 3.4 | 3.0 ± 3.9 | 24.1 ± 30.8 |
| Stem Cell Harvest | | | | | | | |
| 9 | 16 | — | — | 138.8 | 8.7 | 26.8 | 167.5 |
| 10 | 12 | — | — | 150 | 12.5 | 22.2 | 185 |
| 11 | 8 | — | — | 120 | 15 | 8.3 | 103.8 |
| M | 12.0 ± 4.0 | | | 136.3 ± 15.2 | 12.1 | 19.1 ± 9.6 | 152.1 ± 42.7 |

[a]Expansion is expressed relative to starting cell numbers;
[b]The numbers of fungus specific CD4 cells after 21 days of culture was determined by intracellular flow cytometry assessing production of TNFα in response to stimulation with a combination of all fungal lysates;
PBMC—peripheral blood mononuclear cells;
PBSC—peripheral blood stem cells;
NT—not tested due to unavailability of cells for analyses;
M—Mean.

Antihyphal Activity of Panfungal T Cells

Antifungal activity was assessed using a calorimetric assay with 2,3-bis[2-methoxy-4-nitro-5-sulfophenyl]2H-tetrazolium-5-carboxyanilide sodium salt (XTT) and 2-methyl-1,4-napthoquinone (menadione). Working XTT-menadione solution was prepared by combining XTT and menadione stock solutions at a ratio of 4:1.

Fungal spores ($1 \times 10^4$ in 200 µl YPD broth) were germinated at 37° C. in 96-well microculture plates and incubated for 16-28 h (*A. fumigatus* and *L. prolificans*) or 16-20 h (*A. terreus, C. albicans* and *C. krusei*). The hyphal masses were washed twice in PBS by centrifuging at 15,000 g for 15 minutes. PBMC, white blood cells (WBC) and fungus-specific T cells were added to appropriate wells at an effector to target ratio of 5:1 ($5 \times 10^4$ of each cell type) and incubated at 37° C. for 2 hours.

Cells were lysed by washing in sterile water and hyphal masses were resuspended in 200 µl sterile water and 10 µl of XTT-menadione reagent. The plate was vortexed, incubated at 37° C. for 2 hours, then centrifuged at 4,000 g for 10 minutes. The supernatant was collected and absorbance of the XTT reduction product (formazan) measured at 450 nm filter using a 620 nm reference. Absorbance was standardized against unconverted XTT in wells containing only media and XTT/menadione solution. Percent hyphal damage was calculated: % HD=(1-X/C)×100, where X is absorbance of the test well and C is absorbance of the control wells with hyphae only.

Figure 4A:
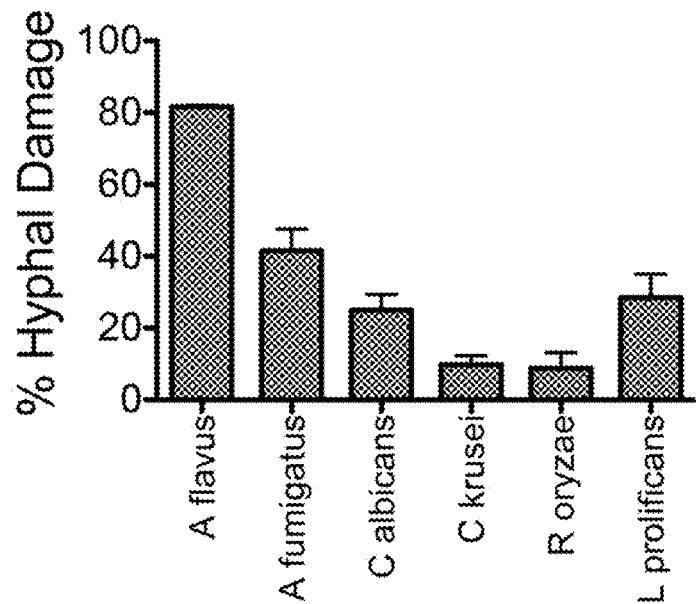
FIG. 4A-FIG. 4B are graphical representations of the antihyphal activity of cultured panfungal T cells as assessed using an XTT calorimetric assay.
Figure 4B:
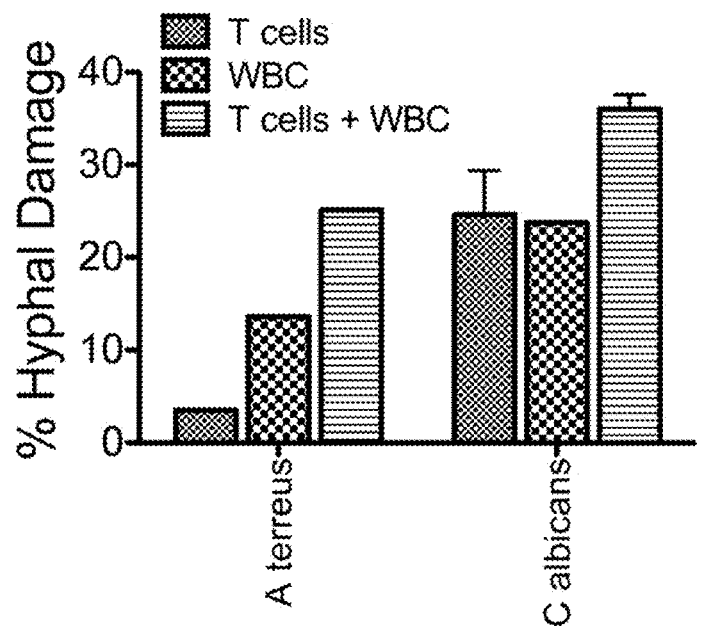

The percentages of hyphal damage towards *A. flavus, C. albicans, C. krusei, R. oryzae* and *L. prolificans* were 81.7±0.6 (n=2), 25.1±9.9 (n=5), 9.8±5.7 (n=5), 8.7±6.3 (n=2), 28.5±14.7 (n=5) respectively (FIG. 4a). The addition of white blood cells at equal numbers with T cells yielded higher antihyphal activity towards both *A. terreus* and *C. albicans* (FIG. 4b).

The Production of Innate Effector Cytokines by Stimulated Panfungal T Cells

Production of innate effector cytokines by panfungal T cells in response to stimulation with MoDC exposed to all fungus-lysate was determined by cytometric bead array. The levels of IFNγ, IL-4, RANTES, IL-17A, IL-2 and MCP-1 were measured in the supernatants of 7 cultures, IL-8 in 6 cultures and MIP-10 in 5 cultures (Table S1). IL-17A and MCP-1 were not detected in either control or fungus-lysate stimulated conditions in 4/7 cultures. IFNγ and IL-2 production was significantly increased, while levels of RANTES, IL-17, MIP-10 and IL-8 were significantly increased following specific stimulation with fungal lysate but were present at lower levels in control cultures. IL-4 or MCP-1 was present in both control and lysate stimulated cultures at the same concentrations.

indicated, MoDC were pre-incubated with 10 μg/ml of HLA-DP (B7/21), -DQ (SPV-L3) or -DR (L243) blocking antibodies at 4° C. for 30 mins prior to using for stimulation. For negative control, cells were stimulated with unexposed MoDC or MoDC exposed to 10 μg/ml lysate from K562 cells. Positive control included cells stimulated with 5 ng/ml phorbol myristate acetate and 1 ng/ml ionomycin. All stimulations were performed for 5 hours at 37° C. in the presence of antibodies to CD28 and CD49d.

To block extracellular release of cytokines, 2 μM Monensin and 1 μg/ml Brefeldin A were added for the last 4 hours of stimulation. Following surface staining, cells were stained for intracellular molecules using the BD fixation and permeabilization kit and antibodies to IFNγ (B27), TNFα (MAb11) and IL-2 (MG1-17H12).

Analyses were performed by flow cytometry. Analyses were based on singlet cells derived from the forward scatter area (FSC-A) and height (-H) flow cytometry dot plots. Fluorescence minus one (FMO) and isotype controls were used to identify positively stained populations. To assess the Th1 cytokine distribution profile of CD4 cells, Boolean analysis was performed. The total number of responding cells and the percentages of cells producing one, two or three cytokines were calculated.

Blockade of HLA-DR, but not HLA-DP or HLA-DQ, on fungal antigen-exposed monocyte-derived dendritic cells (MoDC) significantly reduced the expression of TNFα by CD4$^+$ T cells (FIG. 5a). In addition, the expression of IFNγ, IL-2 by CD4$^+$ cells and the total percentage of responding CD4$^+$ cells was also reduced following blockade of HLA-DR. The reduction was not due to toxicity, as cell viability

TABLE 6

The levels of cytokines measured in the supernatants of panfungal T cells following stimulation

| | | Cytokine level in supernatant (pg/ml) | | | | | | | |
|---|---|---|---|---|---|---|---|---|---|
| | | IFNγ | IL-4 | RANTES | IL-17A | IL-2 | MCP-1 | MIP1β | IL-8 |
| 1 | Control | 0 | 1 | 275 | 0 | 0 | 0 | 1066 | 1170 |
| | Lysate | 75 | 15 | 394 | 0 | 96 | 0 | 1658 | 2574 |
| 2 | Control | 0 | 272 | 192 | 0 | 0 | 212 | NT | 1131 |
| | Lysate | 78 | 261 | 236 | 4 | 759 | 59 | NT | 15180 |
| 5 | Control | 0 | 442 | 678 | 0 | 0 | 0 | 424 | 1342 |
| | Lysate | 28 | 652 | 624 | 7 | 37 | 0 | 424 | 1964 |
| 3 | Control | 2 | 312 | 670 | 0 | 0 | 10 | 643 | 537 |
| | Lysate | 1488 | 420 | 795 | 2 | 823 | 37 | 1790 | 2369 |
| 9 | Control | 0 | 601 | 345 | 0 | 0 | 0 | 362 | 1118 |
| | Lysate | 71 | 818 | 389 | 0 | 61 | 0 | 729 | 1389 |
| 10 | Control | 0 | 0 | 306 | 0 | 0 | 441 | NT | NT |
| | Lysate | 61 | 26 | 300 | 0 | 344 | 310 | NT | NT |
| 11 | Control | 0 | 33 | 334 | 0 | 0 | 0 | 199 | 161 |
| | Lysate | 284 | 34 | 450 | 0 | 112 | 0 | 1553 | 167 |
| mean ± | Control | 0 ± 0 | 237 ± 89 | 400 ± 73 | 0 ± 0 | 0 ± 0 | 221 ± 124 | 539 ± 150 | 910 ± 187 |
| SEM | Lysate | 298 ± 201* | 318 ± 123 | 455 ± 73* | 4 ± 2* | 319 ± 128* | 136 ± 88 | 1231 ± 274* | 3941 ± 2276* |

The levels of innate effector cytokines in the supernatants of panfungal T cell cultures stimulated with MoDC, either unexposed (Control) or exposed to all fungal lysates (Lysate).
The levels of IFNγ (n = 7), IL-4 (n = 7), RANTES (n = 7), IL-17 (n = 3), IL-2 (n = 7), MCP-1 (n = 3) MIP-1β (n = 5) and IL-8 (n = 6) in the supernatants were measured after 5 hours of stimulation.
*p < 0.05 compared with control.

MHC Class II Restriction of Antifungal Responses

To map the antifungal responses to specific MHC class II molecules, the effect of blocking HLA-DR, -DP and -DQ on dendritic cells, on fungus-specific Th1 cytokine production was assessed.

PBMC or cultured T cells were stimulated with antigen-exposed autologous or allogeneic MoDC (using CD14$^+$ cell-derived MoDC) at MoDC to T cell ratios of 1:5. Where was unaffected by the antibodies. To demonstrate that antifungal responses could be mediated through a single shared HLA-DRB1 allele, experiments were performed using MoDC derived from allogeneic donors matched at one HLA-DRB1 allele to present fungal antigens to the expanded T cells. Significant production of TNFα by CD4$^+$ cells was maintained when MoDC derived from partially HLA-DRB1 matched donors were used (FIG. 5b), but not if MoDC from completely HLA-DRB1 mismatched donors were used (FIG. 5c). Similar results were observed in the production of IFNγ and IL-2.

Example 6—Generation of Panfungal Composition to *A. terreus* and *C. krusei*

Cultures are established from unmobilized peripheral blood, G-CSF mobilized peripheral blood stem cell harvests using the *A. terreus* and *C. krusei* lysate combination (10 μg/ml each) for antigen stimulation.

Preparing a composition with T cells reactive to a water soluble lysate of *A. terreus* and a water soluble lysate of *C. krusei* increases the cross-reactivity of the composition.

Analysis of the composition with T cells reactive to *A. terreus* and *C. krusei* is performed as detailed above.

Example 7—Generation of a Panfungal and Panviral Composition

Cultures are established from unmobilized peripheral blood, G-CSF mobilized peripheral blood stem cell harvests using the *A. terreus* and *C. krusei* lysate combination (10 μg/ml each) as described above.

In addition, antigen presenting cells are stimulated by exposure to one or more viral antigens in the form of overlapping peptides from viral proteins, a lysate of virally infected cells, cells genetically engineered with retrovirus, lentivirus or other vectors to express viral proteins. Viral antigens are selected from CMV, EBV, AdV, VZV, influenza, BKV, JC virus, RSV, *parainfluenzae*, rhinovirus, human metapneumovirus, HSV 1, HSV II, HHV6, HHV8, hepatitis A virus, hepatitis B virus, hepatitis C virus, hepatitis E virus, rotavirus, papillomavirus and parvovirus and mixtures thereof (1-100 μg/ml each).

Preparing a composition with T cells reactive to both fungal and viral antigens increases the cross-reactivity of the composition.

Expansion and analysis of the composition is performed as detailed above.

Example 8—Cryopreservation "Banking" of T Cells

Following T lymphocyte harvest, T cells are cryopreserved for adoptive T cell transfer.

A freezing mix containing 40% saline, 40% Albumex20 and 20% DMSO is prepared. The saline is added to the DMSO and chilled before adding the Albumex20. The freezing mix is kept chilled until required.

The cells for cryopreservation are resuspended, pooled and mixed thoroughly. The cells are counted using a haemocytometer and the cell concentration and total cell viability is determined.

The cells are spun at 1400 rpm for 5 mins and 10 mls of the supernatant is removed for sterility and *mycoplasma* testing. The remaining supernatant is discarded.

The cells are washed with up to 200 ml of 0.9% saline supplemented with Albumex20 and spun at 1400 rpm for 5 mins.

The cells are resuspended in 0.9% saline at a concentration of $2 \times 10^7$ cells/ml.

For the cryopreservation of T cells, the maximum volume of cells to be added per bad is to be calculated using the formula:

Maximum volume per bag (mL)=Max number of cells required per bag/$1 \times 10^7$ per ml The number of bags and quality assurance samples to be cryopreserved is determined.

An equal volume of freezing mix is added to the T lymphocyte suspension and mixed. The required volume of cells is transferred into cryopreservation bags and/or vials. The bags and vials are immediately placed into pre-cooled rate controlled freezers to begin cryopreservation.

Example 9—Adoptive Transfer of T Lymphocyte Products

The T cell products are used in adoptive transfer provided they meet the following release criteria:
Greater than 50% post thaw viability;
Less than 2% B cells and monocytes;
Negative for bacterial and fungal contamination at 5 days;
Negative for *Mycoplasma* contamination;
No evidence of alloreactivity defined as <10% specific cytotoxicity against recipient derived PHA blasts at a ratio of 20:1 effector cells to target cells in a standard $^{51}$CR assay;
Non-reactive for infectious disease markers.

Example 10—Adoptive Transfer of Fungal and Panviral Composition

Patients

Twelve patients with a primary diagnosis of malignant disease including acute myeloid leukaemia, acute lymphoblastic leukaemia, lymphoma, chronic lymphocytic leukaemia, and chronic myeloid leukaemia, who were undergoing allogeneic stem cell transplantation, were selected for treatment with T cell compositions reactive to both fungal and viral antigens.

Generation of T Cell Products

T cell cultures were established from HLA-matched donors using an A. *Fumigatus* lysate (10 μg/ml) for antigenic stimulation as described above. In addition, cells were stimulated by exposure to the viral antigens CMV, EBV, AdV, VZV, influenza and BKV (1 μg/ml/viral peptide). T cell cultures were expanded in vitro for a period of up to 17 days and the mean fold increase in cell number was 6.8 fold.

Figure 6:
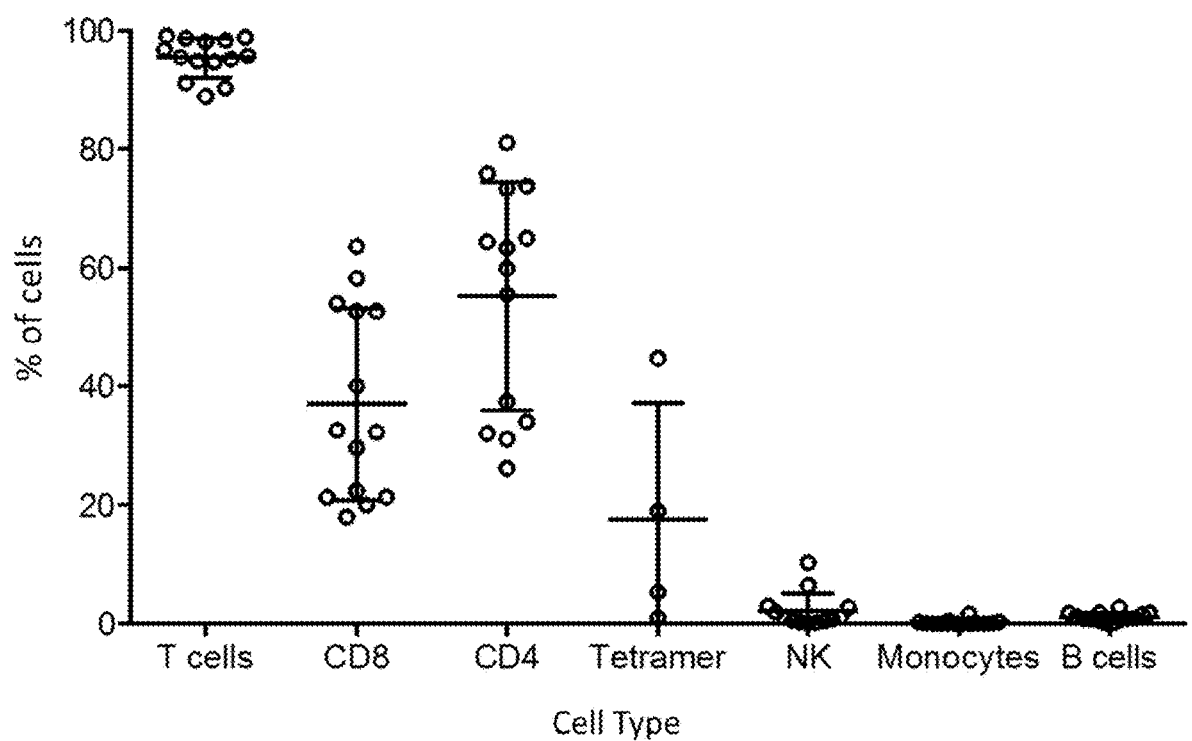
FIG. 6 is a graphical characterisation of the individual T cell product after stimulation with target viral and fungal antigens. Bars represent mean and standard deviations.

All cultures generated >85% T cells. In all T cell cultures the percentage of CD4+ cells, was greater than 25% and comprised less than 2% B cells and monocytes (FIG. 6).

Figure 7:
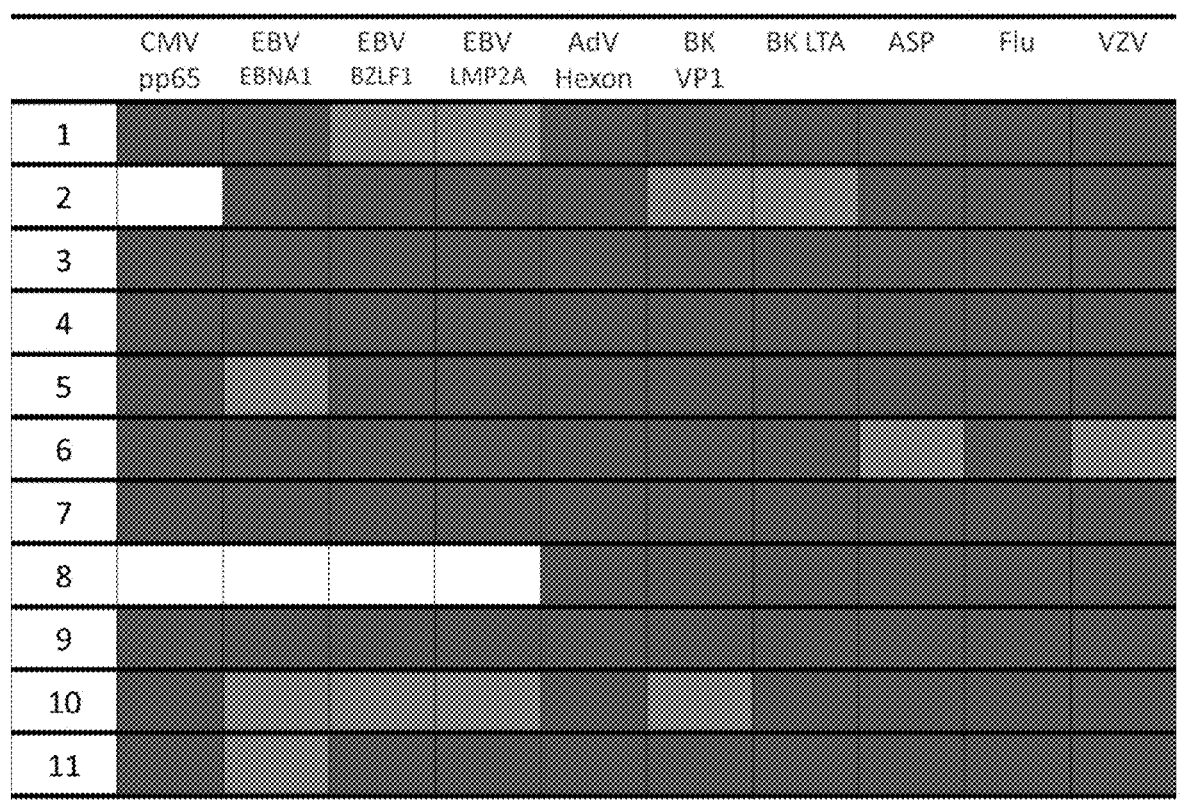
FIG. 7 is a graphical representation of the antigen specificity of individual T cell products to the target antigens as assessed by measuring intracellular expression of the Th1 cytokine IFNγ, following re-stimulation with the same antigens used to originate the T cell culture. Dark grey boxes represent a positive response, light grey boxes no response and a white box indicates that the donor was seronegative for the relevant infection.

At the completion of culture, the presence of fungal or viral-specific T cells was assessed by measuring intracellular expression of the Th1 cytokine IFNγ, following re-stimulation with the same antigens used to originate the T cell culture. The specificity against individual antigens varied between T cell products (FIG. 7). All T cell products showed specificity to lysates derived from AdV and influenza virus. Four T cell products failed to demonstrate specificity for a single antigen and as expected, T cell products derived from CMV or EBV seronegative donors failed to generate T cells specific to those viruses.

These results demonstrate that T cell products reactive to both fungal and viral antigens could be generated from donor samples for adoptive T cell transfer.

Adoptive Transfer of T Cell Products

All patients had received an allogeneic stem cell transplantation. The T cell product was infused prophylactically at a dose of $2 \times 10^7$ cells/m$^2$ post stem cell transplantation (28-76 days post-transplantation). No acute reactions to infusion of the T cell product were observed.

Figure 8:
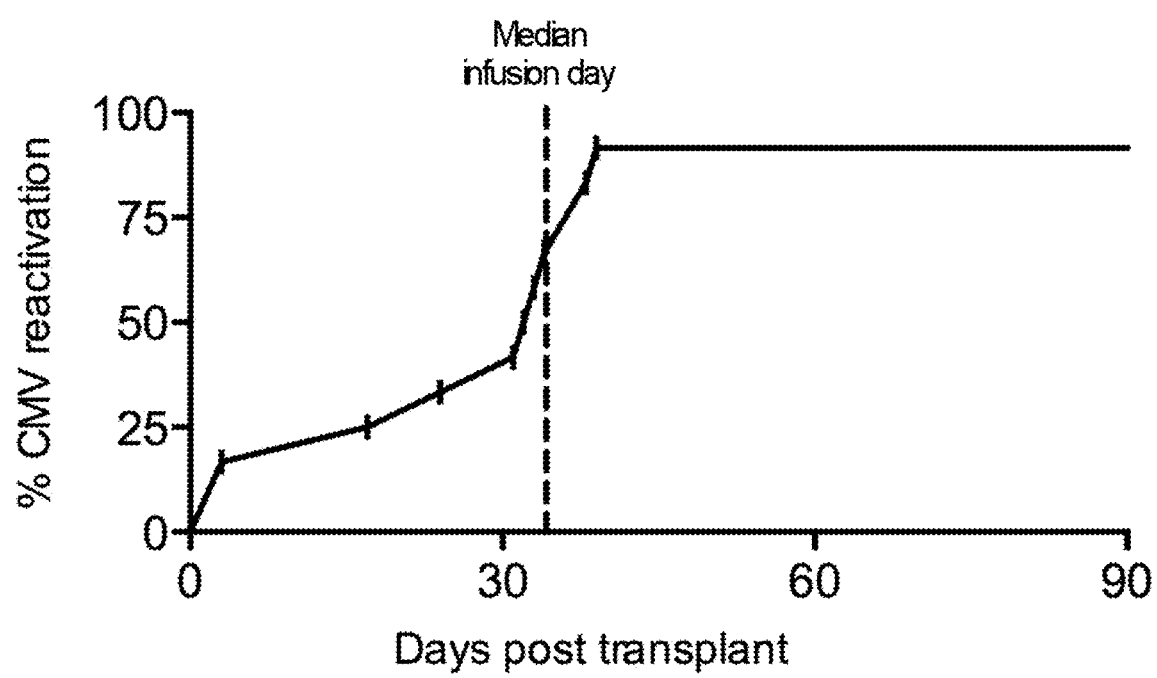
FIG. 8 is a graphical representation of CMV reactivation pre- and post-T cell product infusion.

Patients were monitored for infection by the targeted pathogens. No cases of infection with influenza, AdV, or VZV were identified. Six patients presented with reactivation of EBV infection, four of which were of low quantitation and required no additional therapy. Eleven of the twelve patients had reactivation of CMV infection, with nine occurring prior to T cell infusion (see FIG. 8). These results demonstrate the need for CMV specific T cells to be available soon after stem-cell transplantation.

Figure 9:
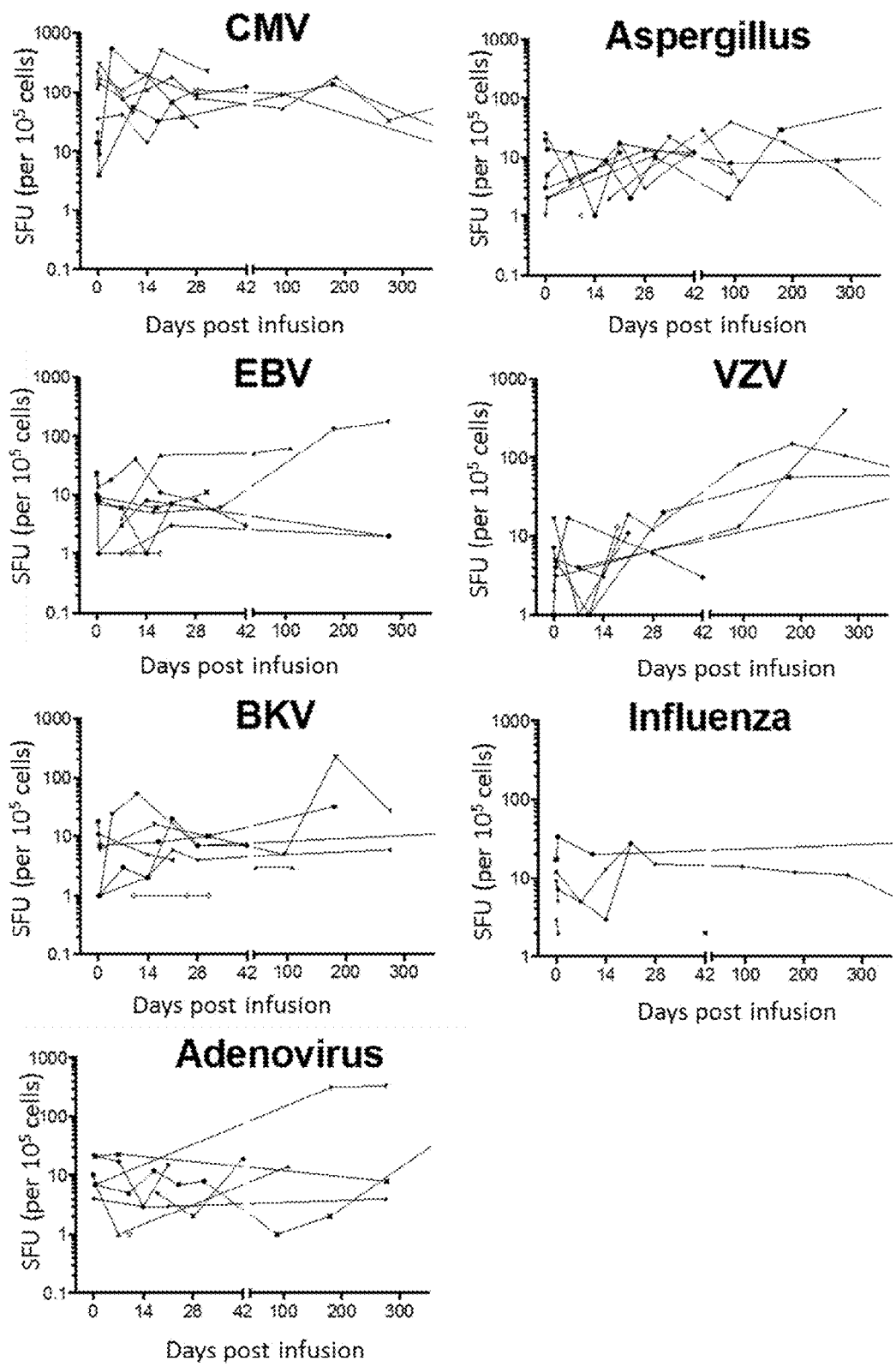
FIG. 9 is a graphical representation of antigen-specific immunity following T cell product infusion as assessed by determining the number of IFNγ spot forming cells against the targeted pathogens (spot forming units per $10^5$ cells).
Figure 10:
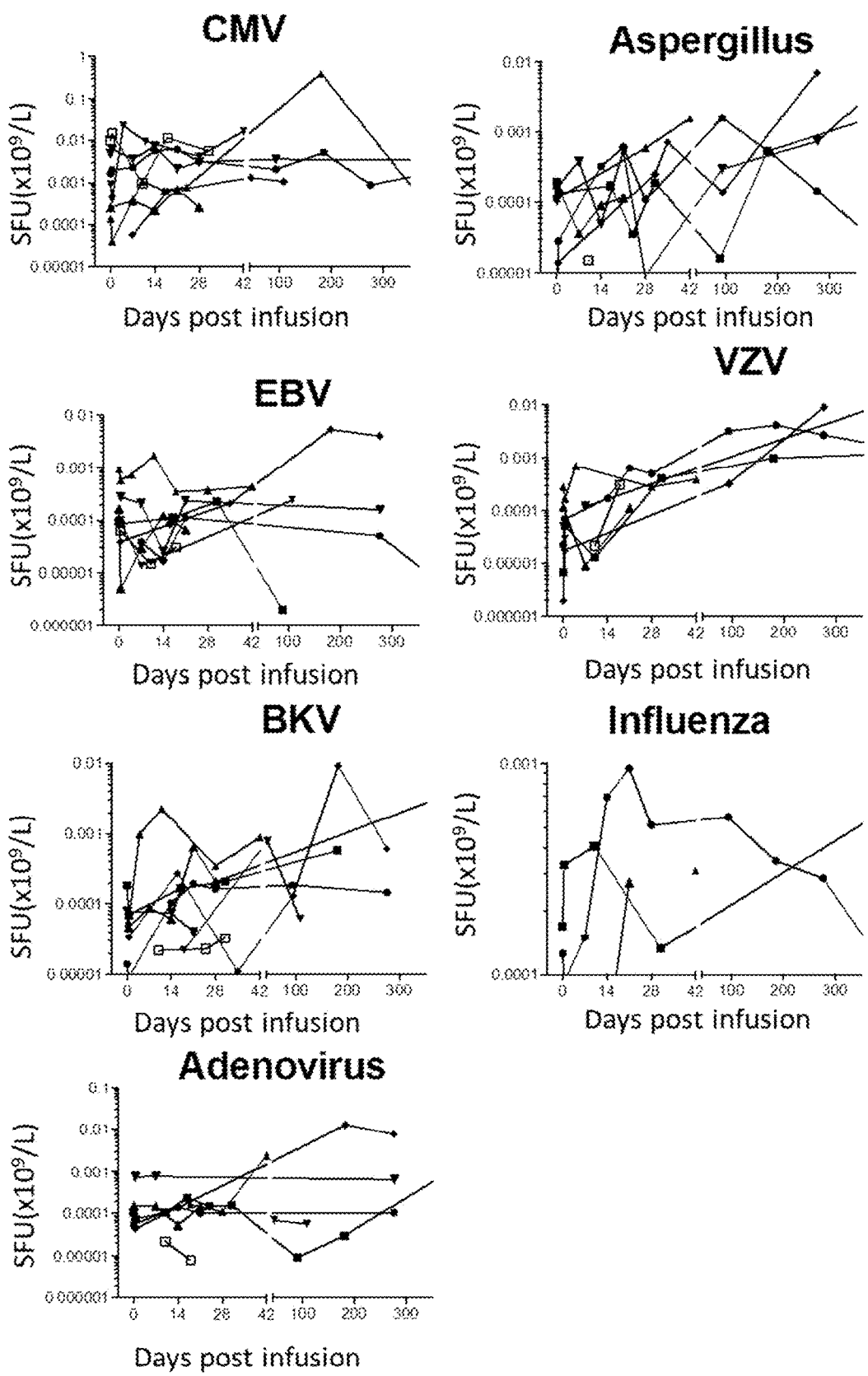
FIG. 10 is a graphical representation of antigen-specific immunity following T cell product infusion as assessed by determining the number of IFNγ spot forming cells against the targeted pathogens (spot forming units per $10^9$ cells).

Antigen specific immunity was assessed following T cell product infusion by determining the number of IFNγ spot forming cells against the targeted pathogens, using methods previously described. Improvement in fungal and viral immunity was observed up to 300 days after infusion of the T cell product when assessed per $10^5$ cells (FIG. 9) and when corrected for increasing overall cell numbers (FIG. 10). These results demonstrate on-going fungal and viral immunity following adoptive transfer of a multi-pathogenic T cell product.

The claims defining the invention are as follows:

1. A composition comprising:
   a water soluble lysate consisting of *Aspergillus terreus*, *Candida krusei*, and *Rhizopus oryzae*;
   a population of antigen presenting cells;
   a population of T cells reactive with *A. terreus*, *C. krusei*, and *R. oryzae*;
   wherein the population of T cells is further reactive with *Aspergillus fumigatus*, *Aspergillus flavus*, *Candida albicans*, *Fusarium oxysporum*, *Fusarium solani*, and *Lomentospora prolificans*.

2. The composition of claim 1, wherein the population of T cells comprises a first population of T cells stimulated in-vitro by antigen presenting cells presenting *A. terreus* antigen, a second population of T cells stimulated in-vitro by antigen presenting cells presenting *C. krusei* antigen, and a third population of T cells stimulated in-vitro by antigen presenting cells presenting *R. oryzae* antigen.

3. The composition of claim 2, wherein the first population of T cells is reactive with *A. fumigatus*, *A. flavus*, *A. terreus*, *F. oxysporum*, *F. solani*, and *L. prolificans*; the second population of T cells is reactive with *A. terreus*, *C. albicans*, and *C. krusei*; and the third population of T cells is reactive with *A. terreus*, *F. oxysporum*, and *R. oryzae*.

4. The composition of claim 1, comprising at least one of the following characteristics:
   at least 80% CD3+ cells;
   at least 70% CD4+ cells;
   at least 30% terminally differentiated effector T cells;
   at least 60% effector memory T cells; and
   less than 10% regulatory T cells.

5. The composition of claim 1, wherein upon administration to a subject, the composition confers a therapeutic or protective immune response against fungi.

6. The composition of claim 2, wherein the population of T cells further comprises a fourth population of T cells reactive with one or more viruses selected from the group consisting of: cytomegalovirus, Epstein-Barr virus, adenovirus, varicella zoster virus, influenza and BK virus, John Cunningham virus, respiratory syncytial virus, *parainfluenzae*, rhinovirus, human metapneumovirus, herpes simplex virus 1, herpes simplex virus II, human herpesvirus 6, human herpesvirus 8, hepatitis A virus, hepatitis B virus, hepatitis C virus, hepatitis E virus, rotavirus, papillomavirus and parvovirus, and mixtures thereof.

7. A method for producing the composition of claim 1, the method comprising:
   contacting a population of T cells with antigen presenting cells previously exposed to a water soluble lysate consisting of *A. terreus*, *C. krusei* and *R. oryzae*.

8. The method of claim 7, wherein the antigen presenting cells are monocytic dendritic cells.

9. The method of claim 7, wherein the water soluble lysate is produced by lysing germinated spores of *A. terreus*, *C. krusei* and *R. oryzae* in water and obtaining the lysate, or wherein the water soluble lysate is obtained by homogenizing germinated spores of *A. terreus*, *C. krusei* and *R. oryzae* in water and obtaining the lysate.

10. The method of claim 7 further comprising:
    contacting the population of T cells with antigen presenting cells which have been previously exposed to:
    a water soluble lysate consisting of *A. fumigatus*, *A. flavus*, *C. albicans*, *F. oxysporum*, *F. solani* and *L. prolificans*; or
    a viral antigen, wherein the viral antigen is a viral protein or a peptide or peptides from a viral protein or is within a lysate of a virus infected cell or is expressed by a cell modified to express the viral antigen.

11. The method of claim 7 further comprising:
    formulating the population of T cells into a pharmaceutically acceptable carrier.

12. A method of treating a subject in need thereof, the method comprising:
    administering the composition of claim 1, wherein the subject is undergoing or is about to commence or has completed chemotherapy and/or hematopoietic stem cell transplantation and/or solid organ transplantation and/or immunoablation therapy and/or has an inherited familial or congenital immunodeficiency syndrome and/or has an acquired immunodeficiency syndrome and/or is receiving or has received immunosuppressive therapy for an immune mediated disease.

13. The method of claim 12 further comprising:
    matching at least one HLA allele in the population of T cells to at least one HLA allele in the subject, wherein the at least one HLA allele is a HLA-DR allele.

14. The method of claim 12, wherein the population of T cells is non-autologous to the subject.

15. A bank comprising one or more compositions of claim 1, wherein the one or more compositions comprise a population of T cells;
    wherein the population of T cells is stimulated in-vitro using antigen presenting cells exposed to a water soluble lysate consisting of *A. terreus*, *C. krusei*, and *R. oryzae*
    wherein the population of T cells is reactive with *A. fumigatus*, *A. flavus*, *A. terreus*, *C. albicans*, *C. krusei*, *F. oxysporum*, *F. solani*, *R. oryzae*, and *L. prolificans*.

16. The bank of claim 15, wherein at least one HLA allele in the population of T cells in each composition in the bank is a HLA-DR allele.

17. A method of treating a subject in need thereof, the method comprising:
    determining an HLA allele of the subject,
    matching the HLA allele of the subject to an HLA allele in the population of T cells in a composition in the bank of claim 15; and
    administering to the subject, a composition comprising a population of T cells having the same HLA allele as that in the subject, wherein the reactivity with the fungi of the population of T cells in the composition is mediated by the HLA allele.

* * * * *